United States Patent [19]

Kita et al.

[11] Patent Number: 5,409,705
[45] Date of Patent: Apr. 25, 1995

[54] PHOSPHOBETAINE AND DETERGENT AND COSMETIC CONTAINING THE SAME

[75] Inventors: Katsumi Kita, Osaka; Mitsuru Uno; Hiroshi Kamitani, both of Wakayama; Yoshiaki Fujikura; Nobutaka Horinishi, both of Chiba; Tomohito Kitsuki, Wakayama; Kazuyasu Imai, Tokyo; Yasushi Kajihara, Saitama, all of Japan

[73] Assignee: Kao Corporation, Tokyo, Japan

[21] Appl. No.: 796,337

[22] Filed: Nov. 22, 1991

[30] Foreign Application Priority Data

| May 20, 1991 | [JP] | Japan | 3-114685 |
| May 20, 1991 | [JP] | Japan | 3-114686 |
| Jun. 19, 1991 | [JP] | Japan | 3-147504 |
| Jun. 19, 1991 | [JP] | Japan | 3-147506 |
| Jul. 1, 1991 | [JP] | Japan | 3-160266 |
| Jul. 4, 1991 | [JP] | Japan | 3-164398 |

[51] Int. Cl.$^6$ ............ C07C 69/76; C07H 15/00; A61K 7/06
[52] U.S. Cl. ............ 424/401; 424/78.02; 424/70.1; 424/70.13; 558/105; 536/17.1; 536/117; 536/17.9
[58] Field of Search ............ 536/17.1, 117, 17.9; 528/398, 399, 400; 558/105, 81; 424/78.02, 78.08, 71, 401; 514/77, 25, 53, 54; 252/174.16, 174.17, 545

[56] References Cited

U.S. PATENT DOCUMENTS

| 3,382,236 | 5/1968 | Guttog | 536/117 |
| 4,215,064 | 7/1980 | Lindemann et al. | 558/105 |
| 4,283,542 | 8/1981 | Lenick, Jr. et al. | 448/81 |
| 4,298,709 | 11/1981 | Ginter et al. | 528/398 |
| 4,416,830 | 11/1983 | Morr et al. | 558/158 |
| 4,650,862 | 3/1987 | Imamura et al. | 536/17.1 |
| 4,731,162 | 3/1988 | Solarek et al. | 536/114 |
| 5,034,519 | 7/1991 | Beuvery et al. | 536/117 |
| 5,066,794 | 11/1991 | Shiba | 536/17.1 |

FOREIGN PATENT DOCUMENTS

| 0312962 | 4/1989 | European Pat. Off. . | |
| 0320942 | 6/1989 | European Pat. Off. | 536/17.1 |
| 2567130 | 1/1986 | France . | |
| 1103031 | 3/1961 | Germany | 528/460 |
| 1156563 | 10/1963 | Germany | 528/400 |
| 63-183594 | 7/1988 | Japan | 536/17.1 |
| 2155017 | 9/1985 | United Kingdom . | |
| 2179661 | 3/1987 | United Kingdom . | |

OTHER PUBLICATIONS

Chemical Abstracts, vol. 188, No. 13, 29 Mar. 1993, Columbus, Ohio, abstract No. 124959, and Jp-A-4 182 492 (Kao Corporation) 30 Jun. 1992.

Chemical Abstracts, vol. 118, No. 23, 7 Jun. 1993, Columbus, Ohio, abstract No. 234409, and JP-A-4 226 996 (Kao Corporation) 17 Aug. 1992.

Chemical Abstracts, vol. 118, No. 9, 1 Mar. 1993, Columbus, Ohio, abstract No. 81326, and JP-A-4 226 998 (Kao Corporation) 17 Aug. 1992.

Primary Examiner—Thurman K. Page
Assistant Examiner—Peter F. Kulkosky
Attorney, Agent, or Firm—Sughrue, Mion, Zinn, Macpeak & Seas

[57] ABSTRACT

A novel phosphobetaine is disclosed. This compound is very excellence in that it exerts a conditioning effect of imparting a good feel to the skin or hair, is excellent in humidifying properties, is available at a low price, and thus it is highly usable in detergents, cosmetics, a bathing preparation and the like. A detergent composition, a cosmetic, and a bathing preparation each containing the phosphobetaine are also disclosed.

8 Claims, 11 Drawing Sheets

PHOSPHOBETAINE AND DETERGENT AND COSMETIC CONTAINING THE SAME

FIELD OF THE INVENTION

This invention relates to a novel phosphobetaine which is useful as, for example, a base, a surfactant, an emulsifier, a conditioning agent or a humectant for hair or skin detergents and cosmetics.

This invention further relates to a detergent composition. More particularly, it relates to a detergent composition which causes neither any excessive removal of the sebum, dry-up nor decrease in the moistness of the skin after washing but imparts a moist feel to the skin or hair.

This invention still further relates to a cosmetic. More particularly, it relates to a cosmetic having excellent humidifying effects, which are scarcely deteriorated by, for example, washing with water, and imparting a less sticky but moist feel to the skin or hair.

BACKGROUND OF THE INVENTION

In general, detergent compositions contain various surfactants in order to improve the washing effects and to give a refreshing feel after washing. For example, alkyl sulfates, polyoxyethylene alkyl sulfates and alkyl benzenesulfonates have been used as a surfactant. However, these surfactants are relatively highly irritative to the skin or hair and the use of them tends to cause excessive removal of the sebum due to the high washing effects thereof, accompanied by dry-up, stretched feel and decrease in the moistness. Because of this, less irritative surfactants such as alkyl phosphates and acylated amino acid salts have been used as a surfactant or an emulsifier in skin or hair detergents or cosmetics.

However, the recent consumers' fondness for high-grade and diversified products has made it necessary to develop a compound which is not only less irritative to the skin, but also exerts a conditioning effect of imparting a preferable feel to the skin or hair and can be blended in skin or hair detergents.

To improve a moist feel of the skin or hair after washing, it has been attempted to use cosmetic lotions or milky lotions containing humectants. It has also been attempted to add humectants to hair or skin detergents such as shampoos in order to impart a moist feel to the hair or skin.

However, since conventional humectants are soluble in water, while the detergents have to be washed away with water after the use, humectants contained in the detergents are also washed away with water. When these humectants are used in such a large amount that sufficient humidifying effects remain after washing away with water, there arises another problem that the feel at the use (for example, stickiness) is worsened.

Therefore, it has been required to develop a detergent composition which exerts sufficient humidifying effects without causing any unpleasant feel such as stickiness.

On the other hand, various humectants exerting protecting effects on the skin or hair have been employed in cosmetics. Examples of humectants which have been employed in practice include propylene glycol, glycerol, urea, sorbitol and alkylene oxide adducts of alcohols.

However, none of these humectants is satisfactory in humidifying properties, hygroscopicity, hygroscopic rate or feel at the use. Although natural polysaccharides such as hyaluronic acid are relatively excellent in humidifying properties and the feel at the use, they are expensive and thus application thereof is exclusively restricted to, for example, relatively high-grade cosmetics.

Accordingly, it has been required to develop a compound which is excellent in humidifying properties, inexpensive and applicable to detergents such as a shampoo or cosmetics such as a hair conditioner and the like.

Furthermore, since conventional humectants are soluble in water, they are prone to be removed from the skin or hair by water or perspiration and thus frequently fail to fully exert the inherent effects when they are used at, for example, swimming pool or when they are contained in cosmetics to washed away with water (for example, hair conditioners and body conditioners). When these humectants are used in such a large amount that sufficient humidifying effects remain after washing away with water, there arises another problem that the feel at the use (for example, stickiness) is worsened.

Therefore, it has also been required to develop a cosmetic which is highly resistant to sweat, can sustain a sufficient humidifying effects after washing with water and impart a less sticky but moist feel.

SUMMARY OF THE INVENTION

It is an object of the present invention to provide a less irritative compound which can exert a conditioning effect of imparting a good feel to the skin or hair, is excellent in humidifying properties and is available at a low price.

It is a further object of the present invention to provide a detergent composition which can impart a less sticky but moist feel to the skin without causing any dry-up or stretched feel of the skin or any creaky feel of the hair.

It is a still further object of the present invention to provide a cosmetic which can exert excellent humidifying effects and impart a softness as well as a less sticky but moist feel to the skin or hair.

Under these circumstances, the present inventors have conducted extensive studies and, as a result, they found that the aforesaid objects can be achieved by using a novel phosphobetaine, thus completing the present invention.

Accordingly, the present invention provides a phosphobetaine represented by the following formula (I):

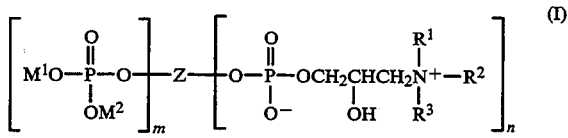

wherein Z represents a residue remaining after eliminating (m+n) hydroxyl group(s) from a polyol;

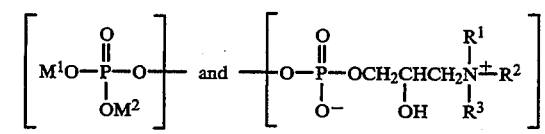

represent each a group bonding to a carbon atom of Z to which the hydroxyl group had bonded;

in which $R^1$, $R^2$ and $R^3$ may be either the same or different from each other and each represents a straight-chain or branched alkyl or alkenyl group having 1 to 24 carbon atoms and optionally having hydroxyl group(s); and $M^1$ and $M^2$ may be either the same or different from each other and each represents a hydrogen atom or a cationic group; provided that, when Z is a hexose residue, at least one of $R^1$, $R^2$ and $R^3$ is a straight-chain or branched alkyl or alkenyl group having 5 to 24 carbon atoms and optionally having a hydroxyl group, or a hydroxyalkyl or hydroxyalkenyl group having 1 to 4 carbon atoms;

m is a number of 0 or above; and n is a number of 1 or above; provided that the sum of m and n is not more than the number of hydroxy groups in the polyol;

as well as a detergent composition and a cosmetic composition each containing the phosphobetaine.

DETAILED DESCRIPTION OF THE INVENTION

Figure 1:
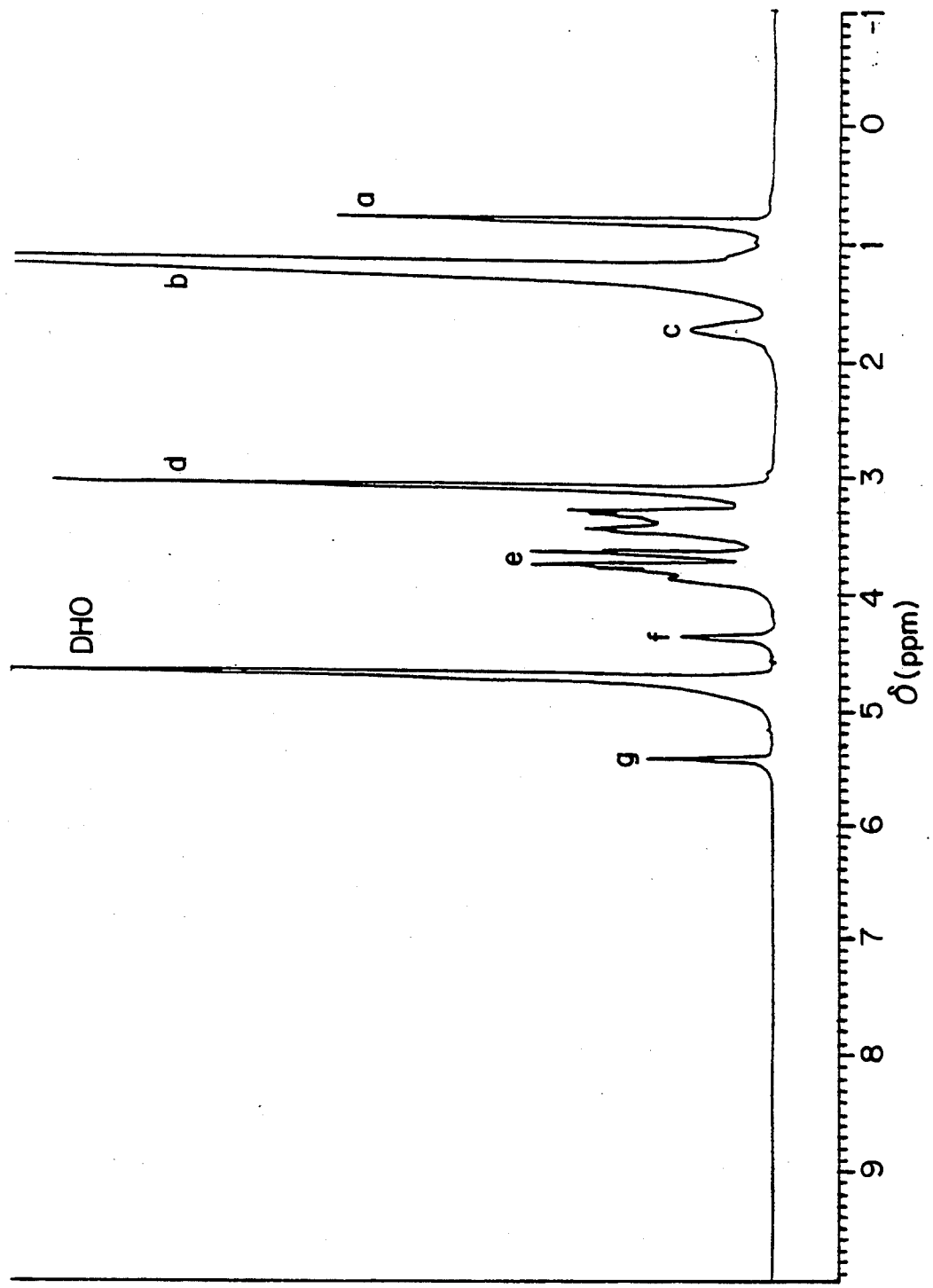
FIG. 1 is the $^1$H-NMR spectrum of α-D-glucopyranose-1-[2-hydroxy-3-(N,N-dimethyl-N-octadecylammonio)propyl]phosphate obtained in Example 4.

There have been already known a sugar phosphobetaine, which has an alkyl group having 1 to 4 carbon atoms but no hydroxyl group, as a compound similar to the phosphobetaine of the above formula (I) of the present invention (refer to JP-A-61-22096, the term "JP-A" as used herein means an "unexamined published Japanese patent application"). However this compound is much inferior to the one of the present invention represented by formula (I) in performance and thus is unavailable in practice as a conditioning agent or a humectant capable of imparting a good feel to the skin or hair. That is to say, it has been found by the present inventors for the first time that the phosphobetaine represented by the above formula (I) has excellent properties as a detergent, an emulsifier, a conditioning agent or a humectant exerting a conditioning or humidifying effect on the hair or skin.

Now the present invention will be described in detail.

The phosphobetaine of the present invention is represented by formula (I). In formula (I), Z represents a residue remaining after eliminating (m+n) hydroxyl groups from a polyol, wherein m and n are as defined above. Useful examples of the polyol to be used in the present invention are those given in the following (a) to (k).

(a) A monosaccharide:

Useful examples of the monosaccharide include hexoses (for example, allose, altrose, galactose, glucose, gulose, idose, mannose, talose, fructose, inositol) and pentoses (for example, arabinose, ribose, deoxyribose, lyxose, ribulose). Further, the hydroxyl groups of these monosaccharides, except at least one, may be modified with appropriate organic residue(s) such as an acyl group having 2 to 24 carbon atoms by acetylation, an alkoxy group having 1 to 24 carbon atoms by etherification, a hydroxypoly (1 to 10 mols)-$C_{2-3}$ alkyleneoxy group by alkylene oxide-addition, a 2-$C_{1-24}$ alkyl-1,3-dioxy group by acetylation, and the like.

(b) An oligosaccharide:

Useful examples of the oligosaccharide include those comprising from 2 to 9 saccharide residues such as maltooligosaccharides (for example, maltose, maltotriose, maltotetraose, maltoheptaose, cyclodextrin), cellooligosaccharides (for example, cyclodextrin, cellobiose, cellotriose, cellotetraose), mannooligosaccacharides (for example, mannobiose, mannotriose, mannotetraose), fructooligosaccharides (for example, fructobiose, fructotriose, fructotetraose), sucrose and lactose. Further, the hydroxyl groups of these oligosaccharides, except at least one, may be modified with appropriate organic residue(s) such as an acyl group having 2 to 24 carbon atoms by acetylation, an alkoxy group having 1 to 24 carbon atoms by etherification, a hydroxypoly (1 to 10 mols)-$C_{2-3}$ alkyleneoxy group by alkylene oxide-addition, a 2-$C_{1-24}$ alkyl-1,3-dioxy group by acetylation, and the like.

(c) A sugar alcohol:

Useful examples of the sugar alcohol include those obtained by reducing monosaccharides (for example, sorbitol, mannitol, galactitol, xylitol, arabinitol, ribitol) and those obtained by reducing oligosaccharides (for example, maltitol). Further, the hydroxyl groups of these sugar alcohols, except at least one, may be modified with appropriate organic residue(s) such as an acyl group having 2 to 24 carbon atoms by acetylation, an alkoxy group having 1 to 24 carbon atoms by etherification, a hydroxypoly (1 to 10 mols)-$C_{2-3}$ alkyleneoxy group by alkylene oxide-addition, a 2-$C_{1-24}$ alkyl-1,3-dioxy group by acetylation, and the like.

(d) Glycerol;

(e) A polysaccharide:

The polysaccharide to be used in the present invention include those comprising at least 10 monosaccharides. The polysaccharides may optionally be substituted by one or more substituents such as an acyl group having 2 to 24 carbon atoms by acetylation, an alkoxy group having 1 to 24 carbon atoms by etherification, a hydroxypoly (1 to 10 mols)-$C_{2-3}$ alkyleneoxy group by alkylene oxide-addition, a 2-$C_{1-24}$ alkyl-1,3-dioxy group by acetylation, and the like.

Useful examples of the polysaccharide comprising at least 10 monosaccharides include starch, amylose, amylopectin, cellulose, dextran, curdlan, pullulan, inulin, galactan, arabinan, agarose, xylan, mannan, chitin, chitosan and alginic acid. In the practice of the present invention, a mixture of polysaccharides differing in the degree of condensation of monosaccharides from each other or a mixture of two or more polysaccharides can be used. For example, natural polysaccharides such as starch or cellulose, each of which is usually in the form of a mixture showing degree of condensation ranging from several hundreds to several millions, are preferable as the polysaccharide to be used in the present invention.

(f) A polyglycerol:

Useful examples of the polyglycerol include those of having a degree of condensation of at least 2, preferably from 2 to 100.

(g) An epichlorohydrin-crosslinked product of saccharide selected from a sugar alcohol, a monosaccharides and an oligosaccharide:

Examples of the sugar alcohol, monosaccharide and oligosaccharide include those as given in (c), (a) and (b) above, respectively.

(h) A compound selected from entaerythritol, dipentaerythritol or an epichlorohydrin-crosslinked product thereof;

(i) A compound selected from an alkylene glycol, a polyalkylene glycol and a polyvinyl alcohol:

Examples of the alkylene glycol include ethylene glycol, propanediol and butanediol. Examples of the polyalkylene glycol include polyethyleneglycol of a degree of condensation of at least 2, such as diethylene glycol and triethylene glycol. Examples of the polyvinyl alcohol include those having a degree of polymerization of from 10 to 5,000.

(j) Ascorbic acid;

(k) Polyol represented by the following formula (V):

$$[R^4O(E^1O)_p]_r G[(OE^2)_q OH]_s \qquad (V)$$

wherein G represents a residue remaining after eliminating (r+s) hydroxyl groups from a monosaccharide, a sugar alcohol, an oligosaccharide, a polysaccharide, a hydrolysate thereof, glycerol, polyglycerol, pentaerythritol or dipentaerythritol; $[R^4(E^1O)_p]$ group represents a group bonding to a carbon atom of G to which the hydroxy group had boded:

in which $R^4$ represents a straight-chain or branched alkyl or alkenyl group having 1 to 24 carbon atoms and optionally having a hydroxyl group; $E^1$ represents an alkylene group having 1 to 5 carbon atoms and optionally having a hydroxyl group and/or an alkyl group having 1 to 5 carbon atoms; and p is a number of 0 to 5;

$[(OE^2)_q OH]$ group represents a group to be bound to the carbon atom to which the hydroxyl groups eliminated in the group G had been bound:

in which $E^2$ represents an alkylene group having 1 to 5 carbon atoms and optionally having a hydroxyl group and/or an alkyl group having 1 to 5 carbon atoms; q is a number of 0 to 5;

r represents a number of 1 or above; and s represents a number of 0 or above; provided that the sum of r and s is not more than the number of the hydroxyl groups in the monosaccharide, sugar alcohol, oligosaccharide, polysaccharide, glycerol, polyglycerol, pentaerythritol or dipentaerythritol.

Examples of the monosaccharide, sugar alcohol, oligosaccharide, polysaccharide and polyglycerol represented by G in formula (V) include those given in (a), (b), (c) and (f) above, respectively.

In the compound of the present invention represented by formula (I), $R^1$, $R^2$ and $R^3$ represent each a straight-chain or branched alkyl or alkenyl group having 1 to 24 carbon atoms and optionally having hydroxyl group(s) and, when Z represents a hexose residue, at least one of $R^1$, $R^2$ and $R^3$ is an alkyl or alkenyl group having 5 to 24 carbon atoms or a hydroxyalkyl or hydroxyalkenyl group having 1 to 4 carbon atoms. Examples of the straight-chain or branched alkyl or alkenyl group having 1 to 24 carbon atoms include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, ethenyl, propenyl, butenyl, pentenyl, hexenyl, hepteyl, octenyl, nonenyl, decenyl, dodecenyl, undecenyl, tridecenyl, tetradecenyl, pentadecenyl, hexadecenyl, heptadecenyl, octadecenyl, nonadecenyl, eicocenyl, heneicocenyl, dococenyl, tricocenyl, tetracocenyl, methylhexyl, ethylhexyl, methylheptyl, ethylheptyl, methylnonyl, methylundecenyl, methylheptadecanyl, hexyldecyl and octyldecyl groups.

Examples of the straight-chain or branched alkyl groups substituted with hydroxyl group(s) include hydroxymethyl, hydroxyethyl, hydroxypropyl, hydroxybutyl, hydroxypentyl, hydroxyhexyl, hydroxyheptyl, hydroxyoctyl, hydroxynonyl, hydroxydecyl, hydroxyundecyl, hydroxydodecyl, hydroxytridecyl, hydroxytetradecyl, hydroxypentadecyl, hydroxyhexadecyl, hydroxyheptadecyl, hydroxyoctadecyl, hydroxynonadecyl, hydroxyeicosyl, hydroxyheneicosyl, hydroxydocosyl, hydroxytricosyl, hydroxytetracosyl, hydroxymethylhexyl, hydroxyethylhexyl, hydroxymethylheptyl, hydroxyethylheptyl, hydroxymethylnonyl, hydroxymethylundecenyl, hydroxymethylheptadecanyl, hydroxyhexyldecyl and hydroxyoctyldecylbutyl groups. Examples of the straight-chain or branched alkenyl group substituted with hydroxyl group(s) include hydroxyethenyl, hydroxypropenyl, hydroxybutenyl, hydroxypentenyl, hydroxyhexenyl, hydroxyheptenyl, hydroxyoctenyl, hydroxynonenyl, hydroxydecenyl, hydroxydodecenyl, hydroxyundecenyl, hydroxytridecenyl, hydroxytetradecenyl, hydroxypentadecenyl, hydroxyhexadecenyl, hydroxyheptadecenyl, hydroxyoctadecenyl, hydroxynonadecenyl, hydroxyeicocenyl, hydroxyheneicocenyl, hydroxydococenyl, hydroxytricocenyl and hydroxytetracocenyl groups.

Examples of the cationic group represented by $M^1$ or $M^2$ include alkali metals (e.g., sodium, potassium and lithium), ammonium group, alkylammonium groups (e.g., alkylammonium groups having 1 to 40 carbon atoms) and trialkanolamine groups (e.g., triethanolamine group and tripropanolamine group). Furthermore, m is a number of 0 or above, while n is a number of 1 or above. It is preferable that m is 0.

The phosphobetaine of formula (I) of the present invention may be obtained by reacting a phosphate represented by the general formula (II) with an epoxy compound represented by formula (III):

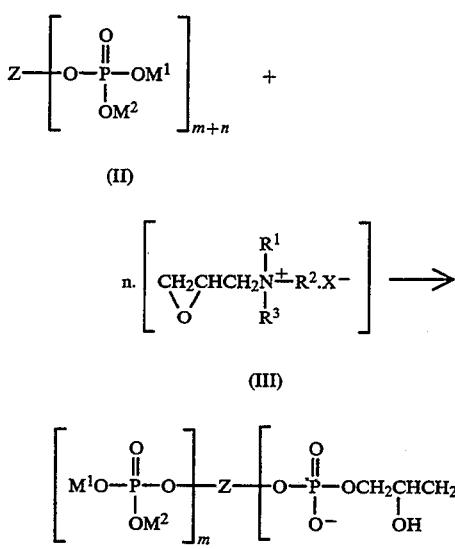

(II)

(III)

(I)

wherein $R^1$, $R^2$, $R^3$, $M^1$ and $M^2$ are each as defined above; and $X^-$ represents an organic or inorganic anionic group.

Examples of the organic anionic group represented by $X^-$ include alkyl sulfates having 1 to 24 carbon atoms and alkyl phosphates having 1 to 24 carbon atoms; and examples of the inorganic anionic group represented by $X^-$ include halogen ions, $\frac{1}{2}SO_4^{2-}$, $NO_3^-$, $\frac{1}{3}PO_4^{3-}$, $\frac{1}{2}HPO_4^{2-}$ and $H_2PO_4^-$.

A specific example of the reaction of the present invention is as follows:

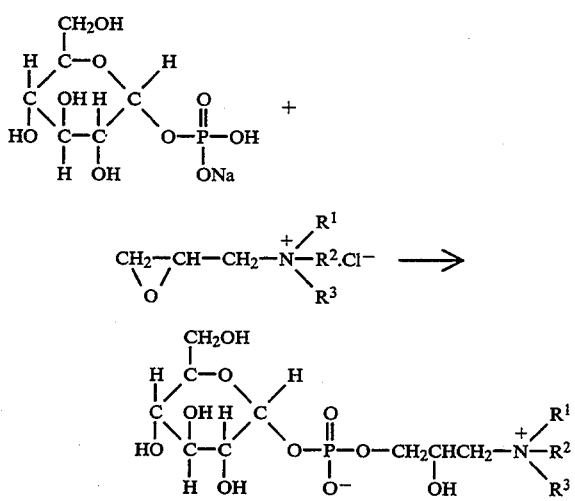

wherein $R^1$, $R^2$ and $R^3$ are each as defined above.

Examples of the phosphate represented by formula (II) include inorganic and organic salts of glucose-1-phosphate, glucose-6-phosphate, mannose-1-phosphate, mannose-6-phosphate, galactose-1-phosphate, galactose-6-phosphate, fructose-1-phosphate, fructose-6-phosphate, fructose-1,6-diphosphate, ribose-1-phosphate, xylose-5-phosphate, inositol phosphate, sucrose phosphate, maltose phosphate, maltotriose phosphate, maltotetraose phosphate, maltopentaose phosphate, maltohexaose phosphate, maltoheptaose phosphate, cyclodextrin phosphate, cellobiose phosphate, lactose phosphate, sorbitol phosphate, mannitol phosphate, galactitol phosphate, xylitol phosphate, arabinitol phosphate, ribitol phosphate, maltitol phosphate, glycerol phosphate and a sugar phosphate represented by the following formula (IV):

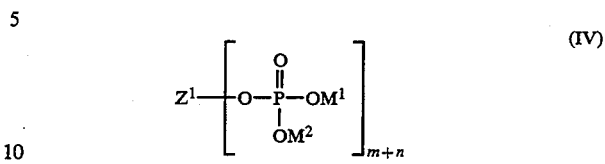

wherein $Z^1$ represents a residue remaining after eliminating (m+n) hydroxyl groups from a polysaccharide having a degree of condensation of the constituting monosaccharides of at least 10 and optionally having substituent(s) or a hydrolysate thereof;

m and n are as defined above; and $M^1$ and $M^2$ are as defined above.

The above-mentioned sugar phosphate (IV) may be easily prepared by reacting a polysaccharide with orthophosphoric acid as described in U.S. Pat. No. 2,824,870 or reacting a polysaccharide with salicyl phosphate as described in JP-A-47-34779. In the case of starch, for example, the reaction can be effected in the following manner (refer to Denpun Kagaku Handbook (Starch Science Handbook), edited by Jiro Futakuni p. 510 (1977).

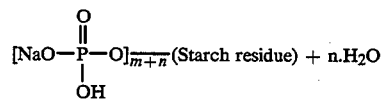

wherein n is as defined above.

The sugar phosphate (IV) may be used in a purified form. Alternately, it may be used as such, i.e., in the form of the reaction product contaminated with diester-type polysaccharide phosphates, which are sometimes formed during the reaction as side products or the unreacted starting polysaccharide.

Further, examples of the phosphate represented by formula (II) include inorganic and organic salts of: phosphates of polyglycerol having a degree of condensation of at least 2; phosphates of epichlorohydrin-crosslinked products of sugar alcohols such as sorbitol, mannitol, maltitol or lactitol; phosphates of epichlorohydrin-crosslinked products of maltooligosaccharides such as maltose or oligosaccharides such as sucrose or lactose; phosphates of pentaerythritol, pentaerythritol condensates or epichlorohydrin-crosslinked products thereof; ethylene glycol phosphate; diethylene glycol phosphate; triethylene glycol phosphate; phosphates of polyethyleneglycol having a degree of condensation of at least 4; propanediol phosphate; and butanediol phosphate. These phosphates (II) may be easily prepared by known methods, for example, the one described in JP-B-50-8052 (the term "JP-B" as used herein means an "examined Japanese patent publication"). Furthermore, when ascobic acid is employed as the polyol, a phosphate of ascorbic acid represented by the following formula (V) is preferably used as the phosphate of formula (II).

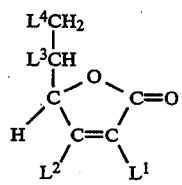

(V)

wherein $L^1$, $L^2$, $L^3$ and $L^4$ may be either the same or different from each other and each represents a hydroxyl group or a group represented by the following formula (VI):

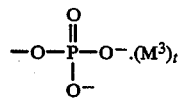

(VI)

wherein t is a number of 2 or 1;
when $t=2$, $M^3$s may be either the same or different from each other and each represents a hydrogen atom or a monovalent cationic group; and when $t=1$, $M^3$ represents a divalent cationic group;
provided that at least one of $L^1$ and $L^2$ is a group of formula (VI).

Examples of the monovalent cationic group represented by $M^3$ include those cited above as the cationic group represented by $M^1$ and $M^2$.

Examples of the ascorbic acid phosphate include ascorbic acid-2-phosphate, ascorbic acid-3-phosphate, ascorbic acid-5-phosphate, ascorbic acid-6-phosphate, ascorbic acid-2,3-diphosphate and ascorbic acid-2,6-diphosphate.

The phosphobetaine of formula (I) may be produced by, for example, reacting the aforesaid phosphate (II) with an epoxy compound (III) in water or a polar solvent such as a lower alcohol (e.g., methanol, ethanol, isopropanol), dimethylformamide and dimethylsulfoxide, or a mixture thereof, preferably in water or a mixture of water with the lower alcohol(s), at a temperature of from 20° to 150° C., preferably from 40° to 90° C., under reduced, normal or increased pressure. Although the reaction can proceed without a catalyst, an acid or alkaline catalyst can be employed if necessary. The amount of the epoxy compound (III) to be used in this reaction may be appropriately determined depending on the values of m and n of the target phosphobetaine (I) of the present invention. In general, the epoxy compound (III) may be preferably used in an amount of from 0.1 to 20 times by mol as much as the number of the phosphate residues (m+n) of the phosphate (II).

In addition to the phosphobetaine (I) of the present invention, the reaction product usually contains inorganic salts formed as side products, the unreacted epoxy compound (III) or an epoxy ring-opened compounds. The content of each component in the reaction products depends on the starting materials, i.e., the phosphate (II) and epoxy compound (III), the mole ratio thereof, the employed solvent and the reaction conditions such as temperature. Therefore, the reaction product may be used as such in some cases. When a product of a higher purity is needed, it may be purified by a common procedure (for example, solvent fraction, dialysis, recrystallization, partition chromatography, ion exchange chromatography, gel filtration).

The phosphobetaine (I) of the present invention thus obtained, which is less irritative to the skin or hair and exerts an excellent conditioning effect, is applicable to a detergent composition such as a hair shampoo, a facial cleanser, a body shampoo, a bar soap, a combination-bar, a dish detergent and the like; and cosmetics such as a rinse, a hair treatment, a body treatment, a cosmetic pack, a cosmetic lotion, cosmetic cream and the like.

When the phosphobetaine (I) of the present invention is used in a detergent composition, it may be contained in an amount of from 0.5 to 50% by weight, preferably from 1 to 30% by weight, based on the total weight of the detergent composition, though it may vary depending on the kinds and amounts of other components. Alternatively, when the phosphobetaine (I) of the present invention is used in a cosmetic, it may be contained in an amount of from 0.1 to 20% by weight, preferably from 0.5 to 10% by weight, based on the total weight of the cosmetic, though it may vary depending on the kinds and amounts of the other components.

The detergent composition of the present invention may arbitrarily contain various surfactants commonly used in detergents such as anionic surfactants, ampholytic surfactants, nonionic surfactants and cationic surfactants, so long as the effects of the present invention are not deteriorated thereby.

Examples of anionic surfactants include sulfate and sulfonate surfactants (e.g., alkyl sulfates, polyoxyethylene alkyl ether sulfates), sulfosuccinate surfactants, taurate surfactants, isethionate surfactants, α-olefinsulfonate surfactants, carboxylate surfactants (e.g., fatty acid soaps, polyoxyethylene alkyl ether carboxylates, acylated amino acid) and phosphate surfactants (e.g., alkyl phosphate).

Examples of ampholytic surfactants include carbobetaine, sulfobetaine and imidazoliniumbetaine surfactants.

Examples of nonionic surfactants include polyoxypropylene-co-polyethylene adduct surfactants, amine oxides surfactants, mono- or diethanolamine surfactants, fatty acid mono- or diethanolamide surfactants, glycerol fatty acid ester surfactants, sucrose fatty acid ester surfactants, alkyl saccharide surfactants and polyhydric alcohol surfactants (e.g., N-polyhydroxyalkyl fatty acid amide).

Examples of cationic surfactants include mono- or dialkyl-addition quaternary ammonium salts having straight-chain or branched alkyl group(s) and those wherein an alkylene oxide is added to the alkyl group(s). It is preferable to use straight-chain alkyl quaternary ammonium salts having 12 to 16 carbon atoms and branched alkyl quaternary ammonium salts having 20 to 28 carbon atoms.

Either one of these surfactants or a combination thereof may be used in the present invention. The surfactant(s) may be contained in the detergent composition of the present invention in an amount of from 2 to 60% by weight, preferably from 10 to 50% by weight, based on the total weight of the composition, though the content thereof may vary depending on the form of the detergent composition. The weight ratio of the surfactant(s) to the phosphobetaine of the present invention may range from 1:2 to 1:50, preferably from 1:3 to 1:30.

In addition to the aforesaid components, the detergent composition of the present invention may optionally comprises additional components commonly employed in detergents, so long as the effects of the present invention are not deteriorated thereby. Examples of the additional components include polyhydric alcohols such as ethylene glycol, diethylene glycol, triethylene glycol and higher polyethyleneglycols, propylene glycol, dipropylene glycol and higher propylene glycols, butylene glycols (e.g., 1,3-butylene glycol, 1,4-butylene glycol), glycerol, diglycerol and higher polyglycerols, sugar alcohols (e.g., sorbitol, mannitol, xylitol, maltitol), ethylene oxide (hereinafter referred to simply as EO) adducts of glycerols, propylene oxide (hereinafter referred to simply as PO) adducts of glycerols, EO and/or PO adducts of sugar alcohols, monosaccharides (e.g., galactose, glucose, fructose) and EO and/or PO adducts thereof and oligosaccharides (e.g., maltose, lactose) and EO and/or PO adducts thereof; oily components such as hydrocarbons (e.g., liquid paraffin, squalane, vaseline, solid paraffin), natural oils (e.g., olive oil, jojoba oil, evening primrose oil, coconut oil, beef tallow), ester oils (e.g., isopropyl myristate, cetyl isooctanoate, neopentyl glycol dicaprate), silicone oils (e.g., dimethyl silicone, methylphenyl silicone) and higher fatty acids (e.g., isostearic acid, oleic acid); medical components such as vitamins, bactericides (e.g., triclosan, triclocarban), antiinflammatory agents (e.g., dipotassium glycyrrhetate, tocopherol acetate), anti-dandruff agents (e.g., zinc pyrithione, octopyrox) and preservatives (e.g., methylparaben, butylparaben); viscosity controllers (e.g., inorganic salts, polyethyleneglycol stearate, ethanol); pearling agents; perfumes; colorants; antioxidants; activators; UV absorbers; water-swelling clay minerals such as montmorrilonite, saponite and hectorite; high molecular compounds such as polysaccharides (e.g., carrageenan, xanthan gum, sodium alginate, pullulan, methyl cellulose, carboxymethyl cellulose, hydroxyethyl cellulose and hydroxypropyl cellulose) and synthetic polymers (e.g., carboxyvinyl polymer and polyvinylpyrrolidone); and pigments such as extender pigments (e.g., titanium oxide, kaolin, mica, sericite, zinc white, talc) and polymethyl methacrylate and nylon powder.

The detergent composition of the present invention may be produced by a conventional method. Although it may be formulated into an arbitrary form (for example, liquid, paste, solid, powder), it may be preferably in the form of a liquid or a paste.

The cosmetic of the present invention may optionally comprises additional components commonly employed in cosmetics in addition to the aforesaid components, so long as the effects of the present invention are not deteriorated thereby. Examples of the additional components include polyhydric alcohols such as ethylene glycol, diethylene glycol, triethylene glycol and higher polyethyleneglycols, propylene glycol, dipropylene glycol and higher propylene glycols, butylene glycols (e.g., 1,3-butylene glycol, 1,4-butylene glycol), glycerol, diglycerol and higher polyglycerols, sugar alcohols (e.g., sorbitol, mannitol, xylitol, maltitol), ethylene oxide (hereinafter referred to simply as EO) adducts of glycerols, propylene oxide (hereinafter referred to simply as PO) adducts of glycerols, EO and/or PO adducts of sugar alcohols, monosaccharides (e.g., galactose, glucose, fructose) and EO and/or PO adducts thereof and oligosaccharides (e.g., maltose, lactose) and EO and/or PO adducts thereof; oily components such as hydrocarbons (e.g., liquid paraffin, squalane, vaseline, solid paraffin), natural oils (e.g., olive oil, jojoba oil, evening primrose oil, coconut oil, beef tallow), ester oils (e.g., isopropyl myristate, cetyl isooctanoate, neopentyl glycol dicaprate), silicone oils (e.g., dimethyl silicone, methylphenyl silicone) and higher fatty acids (e.g., isostearic acid, oleic acid); surfactants such as polyoxyethylen alkyl ethers, polyoxyethylene branched alkyl ethers, polyoxyethylene sorbitan ester, polyoxyethylene glycerol fatty acid esters, polyoxyethylene hydrogenated castor oil, sorbitan ester, glycerol fatty acid esters and polyglycerol fatty acid esters; medical components such as vitamins, bactericides (e.g., triclosan, triclocarban), anti-inflammatory agents (e.g., dipotassium glycyrrhetate, tocopherol acetate), anti-dandruff agents (e.g., zinc pyrithione, octopyrox), preservatives (e.g., methylparaben, butylparaben); foaming promoters (e.g., alkylamine oxides, fatty acid alkanolamides); viscosity controllers (e.g., inorganic salts, polyethyleneglycol stearate, ethanol); pearling agents; perfumes; colorants; antioxidants; activators; UV absorbers; water-swelling clay minerals (e.g., montmorrilonite, saponite, hectorite); high molecular compounds such as polysaccharides (e.g, carrageenan, xanthan gum, sodium alginate, pullulan, methyl cellulose, carboxymethyl cellulose, hydroxyethyl cellulose and hydroxypropyl cellulose) and synthetic polymers (e.g., carboxyvinyl polymer and polyvinylpyrrolidone); and pigments such as extender pigments (e.g., titanium oxide, kaolin, mica, sericite, zinc white, talc) and polymethyl methacrylate and nylon powder.

The cosmetic of the present invention may be produced by a conventional method. Although it may be formulated into an arbitrary form (for example, liquid, cream, solid, powder), it may be preferably in the form of a liquid or a cream.

The novel phosphobetaine (I) of the present invention thus obtained, which is less irritative to the skin or hair and exerts an excellent conditioning effect and humidifying properties, is applicable to detergent compositions (e.g., dish detergents, shampoos), cosmetics (e.g, hair rinses, hair conditioners) and the like. Further, the phosphobetaine of the present invention, wherein an ascorbic acid residue is selected as a polyol residue, is excellent in the compatibility with various cosmetic bases and it is applicable to whitening cosmetics.

Further, the detergent composition of the present invention imparts a less sticky but moist feel to the skin without causing any dry-up or stretched feel of the skin or any creaky feel of the hair. It is appropriately used in, in particular, skin detergents such as a facial cleanser, a body shampoo and a soap, a hair shampoo and a dish detergent.

Furthermore, the cosmetic of the present invention exerts excellent humidifying effects which are hardly deteriorated by sweat or water-washing. It imparts a softness as well as a less sticky but moist feel to the skin or hair. It is suitably used in, in particular, hair conditioner and body conditioner which are to be washed away with water following the application.

To further illustrate the present invention, and not by way of limitation, the following Examples will be given.

EXAMPLE 1

Synthesis of ribose-5-[(2-hydroxy-3-N,N,N-trimethylammonio)-propyl]phosphate 10 g (0.036 mol) of disodium ribose-5-phosphate (manufactured by Sigma Co.), 64 g of water and 36 g of 1N HCl were introduced into a reaction vessel and heated to 60° C. Then a solution of 15 g (0.1 mol) of glycidyltrimethylammonium chloride dissolved in 50 g of ion-exchanged water was added thereto dropwise over 2 hours, while maintaining the reaction system at 60° C. Next, the reaction was carried out for 3 hours at 60° C. After the completion of the reaction, the solvent was distilled off under reduced pressure and the residue was washed with 10 times of ethanol as much as the residue by volume to thereby remove the unreacted glycidyltrimethylammonium chloride. The crude product thus obtained was purified by ion exchange chromatography (ion exchange resin: AG501X8, trade name, manufactured by BIO-RAD Co.). Thus 5.1 g of ribose-5-[(2-hydroxy-3-N,N,N-trimethylammonio)propyl]-phoshpate was obtained (isolation yield: 41%).

$^1$H-NMR (D$_2$O); δ (ppm):

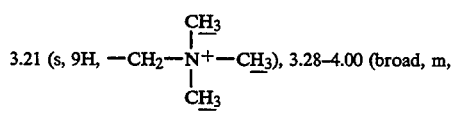

3.21 (s, 9H, —CH$_2$—N$^+$—CH$_3$), 3.28–4.00 (broad, m, 10H, proton originating from the ribose residue and

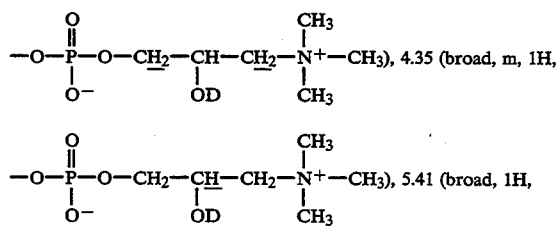

proton bonding to the anomer carbon of the ribose residue)

Mass spectrometry (FAB ionization method):
M/Z346(M+H)$^+$(M=C$_{11}$H$_{24}$O$_9$NP)

EXAMPLE 2

Synthesis of xylose-1-[(2-hydroxy-3-N,N,N-trimethylammonio)-propyl]phosphate 5.0 g (0.012 mol) of di(monocyclohexylammonium) xylose-1-phosphate (manufactured by Sigma Co.), 50 g of water and 12 g of 1N HCl were introduced into a reaction vessel and heated to 60° C. Then a solution of 5.4 g (0.036 mol) of glycidyltrimethylammonium chloride dissolved in 10 g of ion exchanged water was added thereto dropwise over 2 hours, while maintaining the reaction system at 60° C. Next, the reaction was carried out for 3 hours at 60° C. After the completion of the reaction, the solvent was distilled off under reduced pressure and the residue was washed with 10 times of ethanol as much as the residue by volume to thereby remove the unreacted glycidyltrimethylammonium chloride. The crude product thus obtained was purified by ion exchange chromatography (ion exchange resin: AG501X8, trade name, manufactured by BIO-RAD Co.). Thus 1.2 g of xylose-1-[(2-hydroxy-3-N,N,N-trimethylammonio)propyl]phosphate was obtained (isolation yield: 28%).

$^1$H-NMR (D$_2$O): δ (ppm):

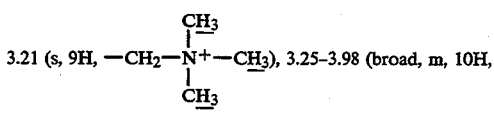

3.21 (s, 9H, —CH$_2$—N$^+$—CH$_3$), 3.25–3.98 (broad, m, 10H, proton originating from the xylose residue and

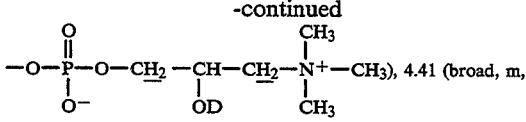

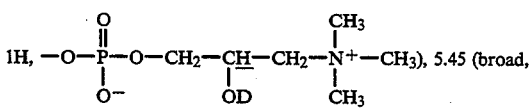

1H, proton bonding to the anomer carbon of the xylose residue)

Mass spectrometry (FAB ionization method):
M/Z346(M+H)$^+$(M=C$_{11}$H$_{24}$O$_9$NP).

EXAMPLE 3

Synthesis of arabinose-5-[(2-hydroxy-3-N,N,N-trimethylammonio)-propyl]phosphate 2.7 g (0.01 mol) of disodium arabinose-5-phosphate (manufactured by Sigma Co.), 50 g of water and 10 g of 1N HCl were introduced into a reaction vessel and heated to 60° C. Then a solution of 3.0 g (0.02 mol) of glycidyltrimethylammonium chloride dissolved in 10 g of ion exchanged water was added thereto dropwise over 2 hours, while maintaining the reaction system at 60° C. Next, the reaction was carried out for 3 hours at 60° C. After the completion of the reaction, the solvent was distilled off under reduced pressure and the residue was washed with 10 times of ethanol as much as the residue by volume to thereby remove the unreacted glycidyltrimethylammonium chloride. The crude product thus obtained was purified by ion exchange chromatography (ion exchange resin: AG501X8, trade name, manufactured by BIO-RAD Co.). Thus 1.1 g of arabinose-5-[(2-hydroxy-3-N,N,N-trimethylammonio)-propyl]phosphate was obtained (isolation yield: 32%).

$^1$H-NMR (D$_2$O); δ (ppm):

3.23 (s, 9H, CH$_2$—N$^+$—CH$_3$), 3.27–4.00 (broad, m, 10H, proton originating from the arabinose residue and

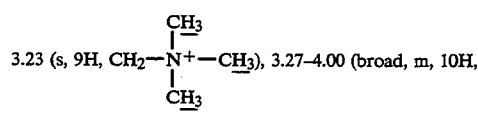

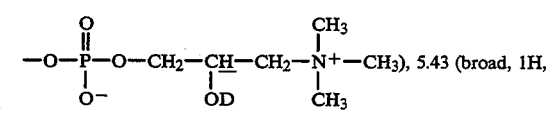

proton bonding to the anomer carbon of the arabinose residue)

Mass spectrometry (FAB ionization method):
M/Z346(M+H)$^+$(M=C$_{11}$H$_{24}$O$_9$NP)

EXAMPLE 4

Synthesis of α-D-glucopyranose-1-[2-hydroxy-3-(N,N-dimethyl-N-octadecylammonio)propyl]phosphate 35 g (0.1 mol) of monosodium α-D-glucose-1-phosphate tetrahydrate and 500 g of water were introduced into a reaction vessl and heated to 60° C. Then a solution of 78 g (0.2 mol) of glycidyldimethyloctadecylammonium chloride dissolved in 200 g of a 30% aqueous solution of ethanol was slowly added thereto dropwise, while maintaining the reaction system at 60° C. Next, the reaction was carried out for 15 hours at 60° C. After the completion of the reaction, the solvent was distilled off under reduced pressure and the residue was washed with 10 times of acetone as much as the residue by volume to thereby remove the unreacted glycidyldimethyloctadecylammonium chloride and epoxy-ring opened product thereof. The crude product thus obtained was purified by recrystallizing from ethanol until a single spot was obtained in thin layer chromatography. Thus 33 g of α-D-glucopyranose-1-[2-hydroxy-3-(N,N-dimethyl-N-octadecylammonio)propyl]phosphate was obtained (isolation yield: 54%).

$^1$H-NMR (D$_2$O) (refer to FIG. 1): δ (ppm): 0.88 (t, 3H, a), 1.28 (broad, 30H, b), 1.77 (m, 2H, c), 3.18 (s, 6H, d), 3.30–4.00 (broad, m, 12H, e), 4.40 (broad, 1H, f), 5.46 (m, 1H, g)

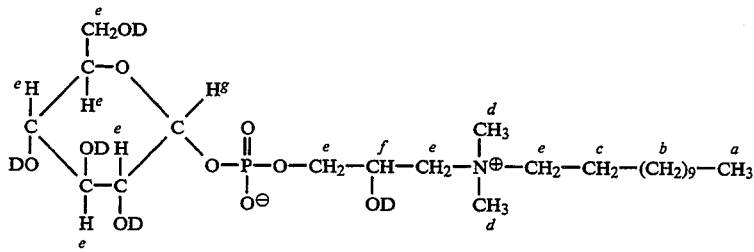

Figure 2:
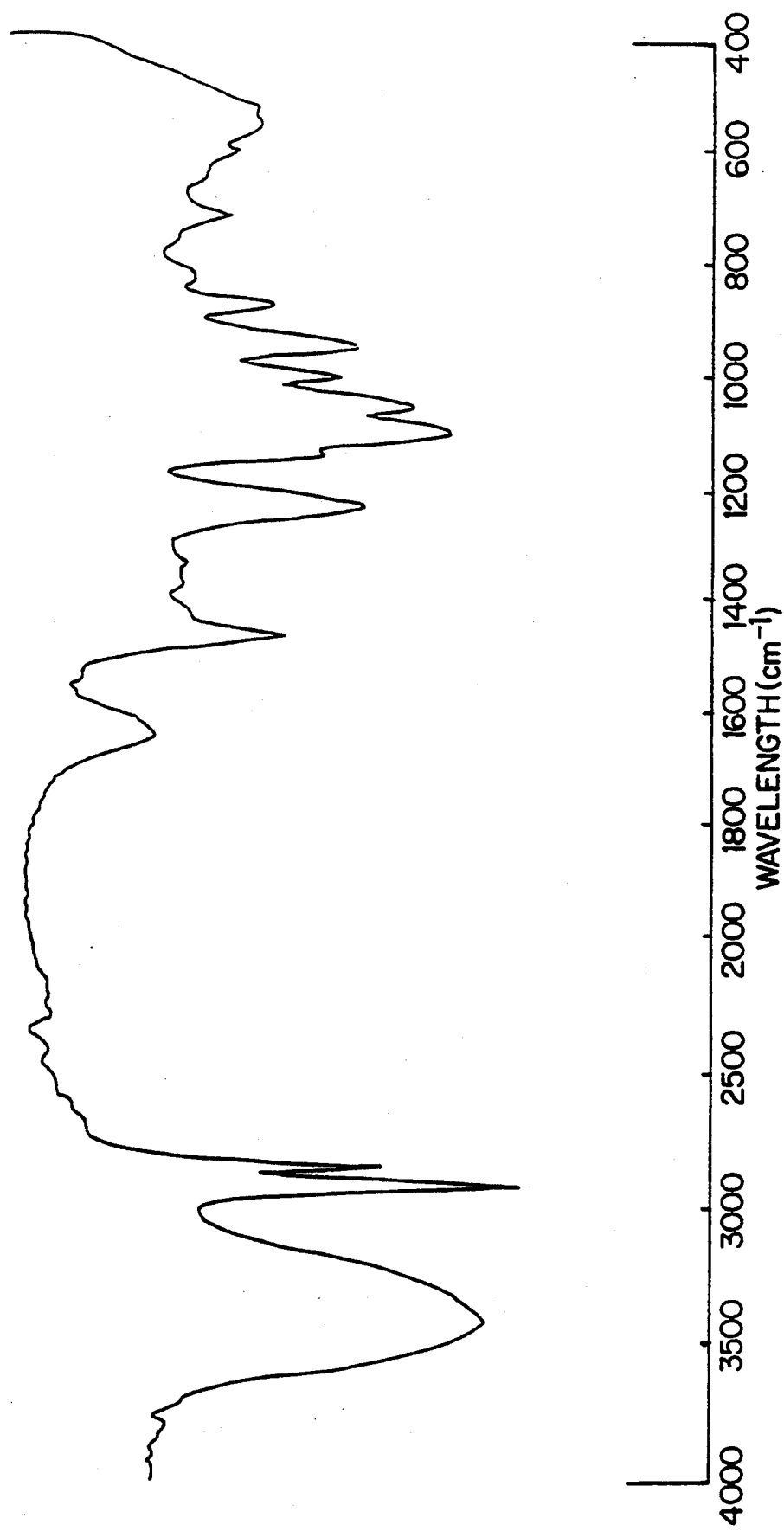
FIG. 2 is the IR spectrum of α-D-glucopyranose-1-[2-hydroxy-3-(N,N-dimethyl-N-octadecylammonio)-propyl]phosphate obtained in Example 4.

IR (KBr pellet method): refer to FIG. 2.
Mass spectrometry (FAB ionization method):
M/Z614(M+H)+(M=C$_{29}$H$_{60}$O$_{10}$NP)

EXAMPLE 5

Synthesis of
α-D-glucopyranose-1-[2-hydroxy-3-(N,N-dimethyl-N-dodecylammonio)propyl]phosphate 35 g (0.1 mol) of monosodium α-D-glucose-1-phosphate tetrahydrate and 500 g of water were introduced into a reaction vessel and heated to 60° C. Then a solution of 61 g (0.2 mol) of glycidyldimethyldodecylammonium chloride dissolved in 200 g of water was slowly added thereto dropwise, while maintaining the reaction system at 60° C. Next, the reaction was carried out for 10 hours at 60° C. After the completion of the reaction, the solvent was removed from the reaction mixture by lyophilization. Then the obtained reaction product was washed with 10 times of ethanol as much as the product by volume to thereby remove the unreacted glycidyldimethyldodecylammonium chloride and the epoxy-ring opened product thereof. The crude product thus obtained was purified by ion exchange chromatography (ion exchange resin: AG501-X8, trade name, manufactured by BIO-RAD Co.) until a single spot was obtained in thin layer chromatography. Thus 22 g of α-D-glucopyranose-1-[2-hydroxy-3-(N,N-dimethyl-N-dodecylammonio)propyl]phosphate was obtained (isolation yield: 42%).

$^1$H-NMR (D$_2$O): δ (ppm): 0.88 (t, 3H, a), 1.32 (broad, 18H, b), 1.76 (m, 2H, c), 3.18 (s, 6H, d), 3.30–4.00 (broad, m, 12H, e), 4.35 (broad, 1H, f), 5.44 (m, 1H, g)

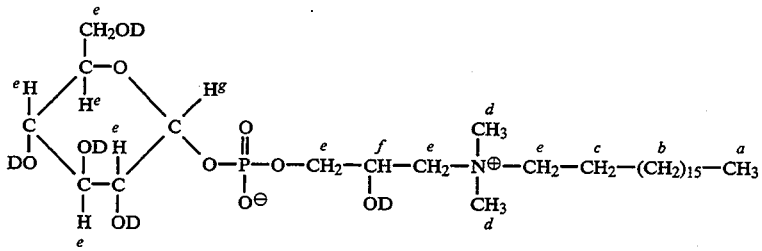

Mass spectrometry (FAB ionization method):
M/Z530(M+H)+(M=C$_{23}$H$_{48}$O$_{10}$NP)

EXAMPLE 6

Synthesis of
α-D-glucopyranose-1-[2-hydroxy-3-(N,N-dimethyl-N-pentylammonio)propyl]phosphate 35 g (0.1 mol) of monosodium α-D-glucose-1-phosphate tetrahydrate and 500 g of water were introduced into a reaction vessel and heated to 60° C. Then a solution of 42 g (0.2 mol) of glycidyldimethylpentylammonium chloride dissolved in 200 g of water was slowly added thereto dropwise, while maintaining the reaction system at 60° C. Next, the reaction was carried out for 10 hours at 60° C. After the completion of the reaction, the solvent was removed from the reaction mixture by lyophilization. Then the obtained reaction product was washed with 10 times of acetone as much as the residue by volume to thereby remove the unreacted glycidyldimethylpentylammonium chloride and the epoxy-ring opened product thereof. The crude product thus obtained was purified by ion exchange chromatography (ion exchange resin: AG501-X8, trade name, manufactured by BIO-RAD Co.). Thus 13 g of α-D-glucopyranose-1-[2-hydroxy-3-(N,N-dimethyl-N-pentylammonio)propyl]phosphate was obtained (isolation yield: 31%).

$^1$H-NMR (D$_2$O): δ (ppm): 0.89 (t, 3H, a), 1.34 (broad, 4H, b), 1.76 (m, 2H, c), 3.19 (s, 6H, d), 3.29–4.02 (broad, 12H, e), 4.38 (broad, 1H, f), 5.43 (m, 1H, g)

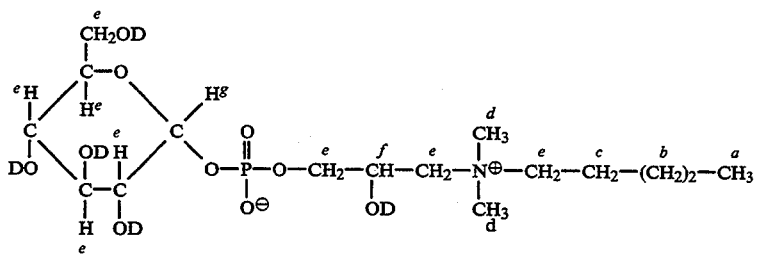

Mass spectrometry (FAB ionization method):
M/Z432(M+H)+ (M=$C_{16}H_{34}O_{10}NP$)

EXAMPLE 7

2,3-dihydroxypropyl[2-hydroxy-3-(N,N-dimethyl-N-pentylammonio)propyl]phosphate 50 g (0.23 mol) of disodium α-glycerophosphate, 500 g of water and 230 g of 1N hydrochloric acid were introduced into a reaction vessel and heated to 60° C. Then a solution of 95.1 g (0.46 mol) of glycidyldimethylpentylammonium chloride dissolved in 400 g of a 30% aqueous solution of ethanol was slowly added thereto dropwise over 5 hours, while maintaining the reaction system at 60° C. Next, the reaction was carried out for 15 hours at 60° C. After the completion of the reaction, the solvent was distilled off under reduced pressure and the residue was washed with 10 times of acetone as much as the residue by volume to thereby remove the unreacted glycidyldimethylpentylammonium chloride and the epoxy-ring opened product thereof. The crude product thus obtained was washed with a 80% aqueous solution of ethanol and then purified until a single spot was obtained in thin layer chromatography. Thus 25 g of 2,3-dihydroxypropyl[2-hydroxy-3-(N,N-dimethyl-N-pentylammonio)propyl]phosphate was obtained in a pure form (isolation yield: 35%).

$^1$H-NMR (D$_2$O): δ (ppm): 0.87 (t, 3H, a), 1.28 (broad, 4H, b), 1.75 (m, 2H, c), 3.17 (s, 6H, d), 3.30–3.90 (m, 11H, e), 4.35 (broad, 1H, f)

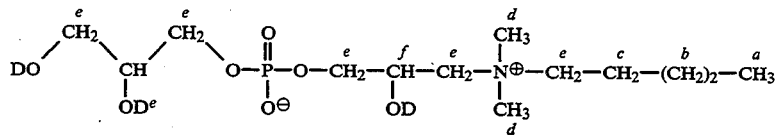

Mass spectrometry (FAB ionization method):
M/Z344(M+H)+ (M=$C_{13}H_{30}O_7NP$)

EXAMPLE 8

Synthesis of
2,3-dihydroxypropyl[2-hydroxy-3-(N,N-dimethyl-N-hexadecylammonio)propyl]phosphate 50 g (0.23 mol) of disodium α-glycerophosphate, 500 g of water and 230 g of 1N hydrochloric acid were introduced into a reaction vessel and heated to 60° C. Then a solution of 166.5 g (0.46 mol) of glycidyldimethylhexadecylammonium chloride dissolved in 600 g of a 30% aqueous solution of ethanol was slowly added thereto dropwise over 3 hours, while maintaining the reaction system at 60° C. Next, the reaction was carried out for 20 hours at 60° C. After the completion of the reaction, the solvent was distilled off under reduced pressure and the residue was washed with 10 times of acetone as much as the residue by volume to thereby remove the unreacted glycidyldimethylhexadecylammonium chloride and the epoxy-ring opened product thereof. The crude product thus obtained was washed with a 90% aqueous solution of ethanol until a single spot was obtained in thin layer chromatography. Thus 53 g of 2,3-dihydroxypropyl[2-hydroxy-3-(N,N-dimethyl-N-hexadecylammonio)propyl]phosphate was obtained in a pure form (isolation yield: 46%).

$^1$H-NMR (D$_2$O): δ (ppm): 0.88 (t, 3H, a), 1.28 (broad, 26H, b), 1.75 (m, 2H, c), 3.16 (s, 6H, d), 3.30–4.00 (m, 11H, e), 4.36 (broad, 1H, f)

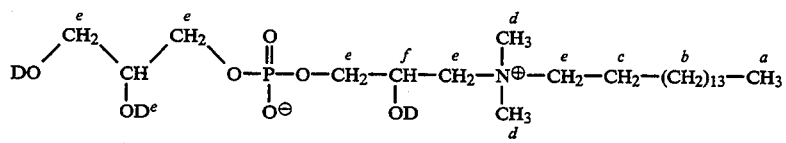

Mass spectrometry (FAB ionization method):
M/Z498(M+H)+ (M=$C_{24}H_{52}O_7NP$)

EXAMPLE 9

Synthesis of
2,3,4,5,6-pentahydroxyhexyl[2-hydroxy-3-(N,N-dimethyl-N-hexadecylammonio)propyl]phosphate 8.9 g (0.032 mol) of sodium salt of sorbitolphosphate prepared in accordance with Synthetic Example 1 as will be given below and 100 g of water were introduced into a reaction vessel and heated to 60° C. Then a solution of 17.4 g (0.048 mol) of glycidyldimethylhexadecylammonium chloride dissolved in 100 g of a 30% aqueous solution of ethanol was slowly added thereto dropwise over 2 hours, while maintaining the reaction system at 60° C. Next, the reaction was carried out for 10 hours at 60° C. After the completion of the reaction, the solvent was distilled off under reduced pressure and the residue was washed with 10 times of acetone as much as the residue by volume to thereby remove the unreacted glycidyldimethylhexadecylammonium chloride and the epoxy-ring opened product thereof. The crude product thus obtained was washed with a 90% aqueous solution of ethanol and then purified in the similar method as described in Example 6 until a single spot was obtained in thin layer chromatography. Thus 5.6 g of 2,3,4,5,6-pentahydroxyhexyl[2-hydroxy-3-(N,N-dimethyl-N-hexadecylammonio)propyl]phosphate was obtained in a pure form (isolation yield: 30%).

$^1$H-NMR (D$_2$O): δ (ppm): 0.87 (t, 3H, a), 1.29(broad, 26H, b), 1.75 (m, 2H, c), 3.16 (s, 6H, d), 3.20–4.00 (m, 14H, e), 4.34 (broad, 1H, f)

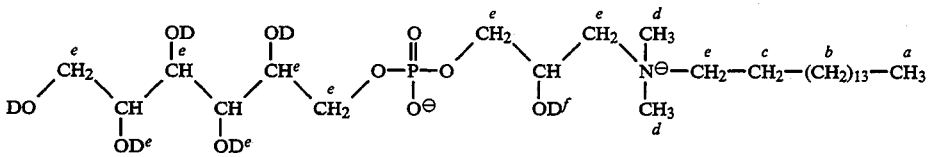

Mass spectrometry (FAB ionization method):
M/Z588(M+H)+(M=C$_{27}$H$_{58}$O$_{10}$NP)

EXAMPLE 10

Synthesis of 2,3,4,5,6-pentahydroxyhexyl[2-hydroxy-3-(N,N-dimethyl-N-pentylammonio)propyl]phosphate 8.9 g (0.032 mol) of sodium salt of sorbitol phosphate prepared in accordance with Synthetic Example 1 as will be given below and 100 g of water were introduced into a reaction vessel. After adjusting the pH value to 6.5 with a dilute hydrochloric acid, the solution was heated to 60° C. Then a solution of 10 g (0.048 mol) of glycidyldimethylpentylammonium chloride dissolved in 100 g of a 30% aqueous solution of ethanol was slowly added thereto dropwise over 2 hours, while maintaining the reaction system at 60° C. Next, the reaction was carried out for 9 hours at 60° C. After the completion of the reaction, the solvent was distilled off under reduced pressure and the residue was washed with 10 times of acetone as much as the residue by volume to thereby remove the unreacted glycidyldimethylpentylammonium chloride and the epoxy-ring opened product thereof. The crude product thus obtained was washed with a 90% aqueous solution of ethanol and then purified in the similar method as described in Example 6 until a single spot was obtained in thin layer chromatography. Thus 3.3 g of 2,3,4,5,6-pentahydroxyhexyl[2-hydroxy-3-(N,N-dimethyl-N-pentylammonio)propyl]phosphate was obtained in a pure form (isolation yield: 30%).

$^1$H-NMR (D$_2$O): δ (ppm): 0.87 (t, 3H, a), 1.28 (broad, 4H, b), 1.75 (m, 2H, c), 3.17 (s, 6H, d), 3.35–3.90 (m, 14H, e), 4.35 (broad, 1H, f)

EXAMPLE 11

Synthesis of maltose[2-hydroxy-3-(N,N-dimethyl-N-dodecylammonio)propyl]phosphate 47 g (0.1 mol) of maltose phosphate disodium salt prepared in accordance with Synthetic Example 2 as will be given below, 400 g of water and 100 g of 1N hydrochloric acid were introduced into a reaction vessel, dissolved by stirring and then heated to 70° C. Then a solution of 122 g (0.4 mol) of glycidyldimethyldodecylammonium chloride dissolved in 300 g of water was slowly added thereto and then the reaction was carried out at 70° C. for 20 hours. After the completion of the reaction, the solvent was removed from the reaction mixture by lyophilization. The reaction product thus obtained was washed with 10 times of acetone as much as the product to thereby remove the unreacted glycidyldimethyldodecylammonium chloride and the epoxy-ring opened product thereof.

After purifying by ion exchange chromatography (ion exchange resin: AG501-X8, trade name, manufactured by BIO RAD Co.), 35 g of maltose[2-hydroxy-3-(N,N-dimethyl-N-dodecylammonio)propyl]phosphate was obtained (isolation yield: 51%).

$^1$H-NMR (D$_2$O): δ (ppm):

0.87 (t, 3H, —CH$_2$C$\underline{H}_3$), 1.32 (broad, 18H,

—CH$_2$—(C$\underline{H}_2$)$_9$—CH$_3$), 1.73 (broad, 2H,

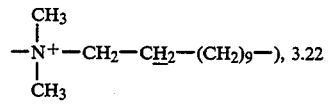

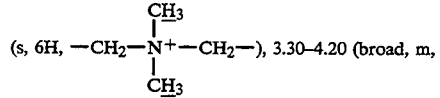

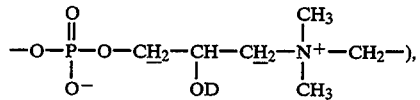

18H, protons originating from the maltose residue, except those bonding to the anomer carbon, and

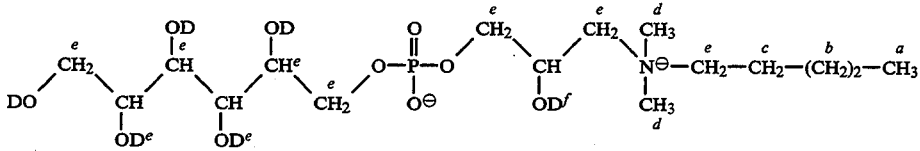

Mass spectrometry (FAB ionization method):
M/Z434(M+H)+(M=C$_{16}$H$_{36}$O$_{10}$NP)

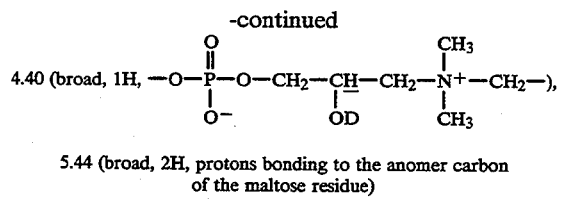

4.40 (broad, 1H)

5.44 (broad, 2H, protons bonding to the anomer carbon of the maltose residue)

Mass spectrometry (FAB ionization method);
M/Z692(M+H)+ (M=$_{29}H_{58}O_{15}NP$)

EXAMPLE 12

Synthesis of fructose-1,6-di[2-hydroxy-3-(N,N-dimethyl-N-pentylammonio)propyl]phosphate 45 g (0.09 mol) of fructose-1,6-diphosphate trisodium salt hexahydrate and 200 g of water were introduced into a reaction vessel and heated to 60° C. Then a solution of 84 g (0.4 mol) of glycidyldimethylpentylammonium chloride dissolved in 200 g of water was slowly added thereto, while maintaining the reaction system at 60° C. Next, the reaction was carried out at 60° C. for 20 hours. After the completion of the reaction, the solvent was removed from the reaction mixture by lyophilization. The reaction product thus obtained was washed with 10 times of acetone as much as the product by volume to thereby remove the unreacted glycidyldimethylpentylammonium chloride and the epoxy-ring opened product thereof. After purifying by ion exchange chromatography (ion exchange resin: AG501-X8, trade name, manufactured by BIO-RAD Co.) until a single spot was obtained in thin layer chromatography, 32 g of fructose-1,6-di[2-hydroxy-3-(N,N-dimethyl-N-pentylammonio)propyl]phosphate was obtained (isolation yield: 52%).

$^1$H-NMR (D$_2$O); δ (ppm): 0.88 (t, 6H, a), 1.31 (broad, 8H, b), 1.76 (m, 4H, c), 3.19 (s, 12H, d), 3.28–4.00 (broad, 19H, e), 4.35 (broad, 2H, f)

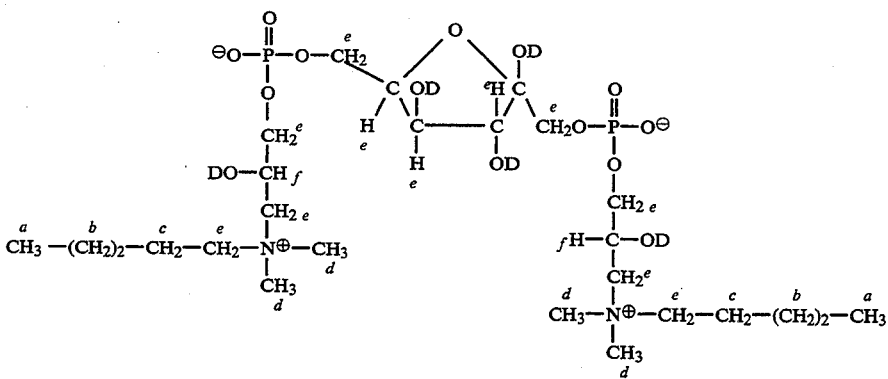

Mass spectrometry (FAB ionization method):
M/Z683(M+H)+ (M=$C_{29}H_{58}O_{15}NP$)

SYNTHETIC EXAMPLE 1

Synthesis of sorbitol phosphate sodium salt:
Sorbitol phosphate sodium salt was prepared by a conventional method (refer to JP-B-50-8052). Namely, 45.5 g of sorbitol was dissolved in 125 ml of water. Then 38.4 g of phosphorus oxychloride was added thereto dropwise over 2 hours under stirring at 0° to 5° C.

During this period, a 10N aqueous solution of caustic soda was added to thereby continuously maintain the pH value of the reaction mixture at 13.5. After the completion of the addition of phosphorus oxychloride, the alkali was further added until no change in pH value was observed any more. Then the reaction mixture was neutralized with the use of a cation exchange resin (Dowex 50×4H+ type, trade name, manufactured by Dow Chemical Co.) and concentrated under reduced pressure, followed by adjusting the pH value to 10 with an aqueous solution of caustic soda. Next, 120 ml of ethanol was added thereto and the inorganic salt thus precipitated was filtered off. Thus the filtrate separated into two phases and the lower one was recovered. Water was added thereto so as to adjust the volume to 250 ml and 1 l of methanol was further added. The sorbitol phosphate sodium salt thus precipitated was collected by filtration and then dried.

This crude product was dissolved in 100 ml of water again and reprecipitated by adding ethanol. Thus 45 g of purified sorbitol phosphate sodium salt was obtained.

SYNTHETIC EXAMPLE 2

Synthesis of maltose phosphate disodium salt:
Maltose phosphate disodium salt was prepared by a conventional method (refer to JP-B-50-8052).
Namely, the procedure of the above Synthetic Example 1 was repeated except that 85.4 g of maltose was dissolved in 250 ml of water. Thus 60 g of purified maltose phosphate disodium salt was obtained.

COMPARATIVE EXAMPLE 1

α-D-glucopyranose-1-[2-hydroxy-(N,N,N-trimethylammonio)propyl]phosphate was prepared as a sugar phosphobetaine having alkyl groups containing 1 to 4 carbon atoms but no hydroxyl group, by a conventional method (refer to JP-A-61-22096).

Namely, 100 g of α-D-glucose-1-phosphate disodium salt, 100 g of water and 70 g of 4N hydrochloric acid were introduced into a reaction vessel and heated to 60° C. Then a solution of 160 g of glycidyltrimethylammonium chloride dissolved in 140 g of water was slowly added thereto, and the reaction was carried out at 60° C. for 4 hours. After the completion of the reaction, the reaction mixture was filtered to thereby remove the suspending impurities. Next, the solution was passed through an electric dialyzer so as to desalt ionic impurities. After removing water from the reaction mixture, 77 g of α-D-glucopyranose-1-[2-hydroxy-(N,N,N-trimethylammonio)propyl]phosphate was obtained.

TEST EXAMPLE 1

By using the compounds of the present invention obtained in Examples 6, 8, 9, 12, 13, 19, 20, hair conditioning agents of the formulations specified in Table 1 were produced. The conditioning effects of these products were examined by the following method. Further, the conditioning effects of the comparative products were similarly examined. Table 1 summarizes the results.

Production Method

Each component was added to water heated to 70° C. and mixed by stirring. Then the obtained mixture was cooled to room temperature under stirring to thereby give a hair conditioning agent.

Evaluation Method 20 g (length: 15 cm) of the hair of a female Japanese, which had been never permed or bleached, was bundled. The obtained hair bundle was shampooed with a marketed shampoo mainly comprising anionic surfactants. Next, 2 g of each conditioning agent listed in Table 1 was uniformly applied thereto. After rinsing with running water for 30 seconds, the hair bundle was dried with towel. Then the softness, smoothness and moist feel of the hair bundle, which was in a moist state, were organoleptically evaluated based on the following criteria:
A: very good;
B: good;
C: moderate; and
D: poor.

EXAMPLE 13

Synthesis of α-D-glucopyranose-1-[2-hydroxy-3-{N-(2-hydroxyethyl)-N,N-dimethylammonio}propyl]phosphate 105 g (0.3 mol) of α-D-glucose-1-phosphate monosodium salt and 500 g of water were introduced into a reaction vessel and heated to 60° C. Then a solution of 164 g (0.9 mol) of glycidyl-2-hydroxyethyldimethylammonium chloride dissolved in 150 g of water was slowly added thereto, while maintaining the reaction system at 60° C. Next, the reaction was carried out at 60° C. for 15 hours. After the completion of the reaction, the solvent was distilled off under reduced pressure and the residue thus obtained was washed with 10 times of ethanol as much as the residue by volume to thereby remove the unreacted glycidyl-2-hydroxyethyldimethylammonium chloride and the epoxy-ring opened product thereof. The crude product thus obtained was dissolved in 300 g of water and purified by ion exchange chromatography (ion exchange resin: AG501-X8, trade name, manufactured by BIO-RAD Co.). Thus, 82 g of α-D-glucopyranose-1-[2-hydroxy-3-{N-(2-hydroxyethyl)-N,N-dimethylammonio}propyl]phosphate was obtained (isolation yield: 68%).

This product was a hygroscopic, grease-like and colorless solid showing a purity of 99% when examined with HPLC (column: TSK-GEL G2500PW, trade name, manufactured by Tosoh Co.; eluent: water).

$^1$H-NMR (D$_2$O); δ (ppm): 3.20 (s, 6H, a), 3.39–3.94 (broad, m, 12H, b), 4.05 (t, 2H, c), 4.40 (broad, 1H, d), 5.45 (m, 1H, e)

TABLE 1

|  | Product of the Invention | | | | | | | Comparative Product | |
|---|---|---|---|---|---|---|---|---|---|
|  | 1 | 2 | 3 | 4 | 5 | 6 | 7 | 1 | 2 |
| Formulation (% by weight) | | | | | | | | | |
| Compound of Example 6 |  | 3.0 |  |  |  |  |  |  |  |
| Compound of Example 8 |  |  |  | 3.0 |  |  |  |  |  |
| Compound of Example 9 |  |  |  |  | 3.0 |  |  |  |  |
| Compound of Example 12 |  |  |  |  |  |  | 3.0 |  |  |
| Compound of Example 13 | 3.0 |  |  |  |  |  |  |  |  |
| Compound of Example 19 |  |  |  |  |  | 3.0 |  |  |  |
| Compound of Example 20 |  |  | 3.0 |  |  |  |  |  |  |
| Glucose |  |  |  |  |  |  |  | 3.0 |  |
| Compound of Comparative Example 1 |  |  |  |  |  |  |  |  | 3.0 |
| Cetyl alcohol | 4.0 | 4.0 | 4.0 | 4.0 | 4.0 | 4.0 | 4.0 | 4.0 | 4.0 |
| Stearyltrimethylammonium chloride | 2.0 | 2.0 | 2.0 | 2.0 | 2.0 | 2.0 | 2.0 | 2.0 | 2.0 |
| Ion exchanged water | 91.0 | 91.0 | 91.0 | 91.0 | 91.0 | 91.0 | 91.0 | 91.0 | 91.0 |
| Evaluation | | | | | | | | | |
| Softness | A | A | A | A | A | A | A | D | C |
| Smoothness | A | B | B | A | A | B | B | D | C |
| Moist feel | B | B | A | A | A | A | B | C | C |

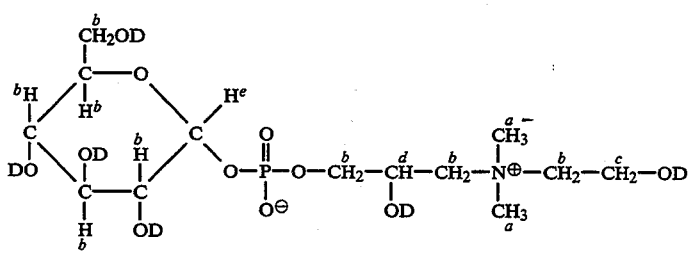

Figure 3:
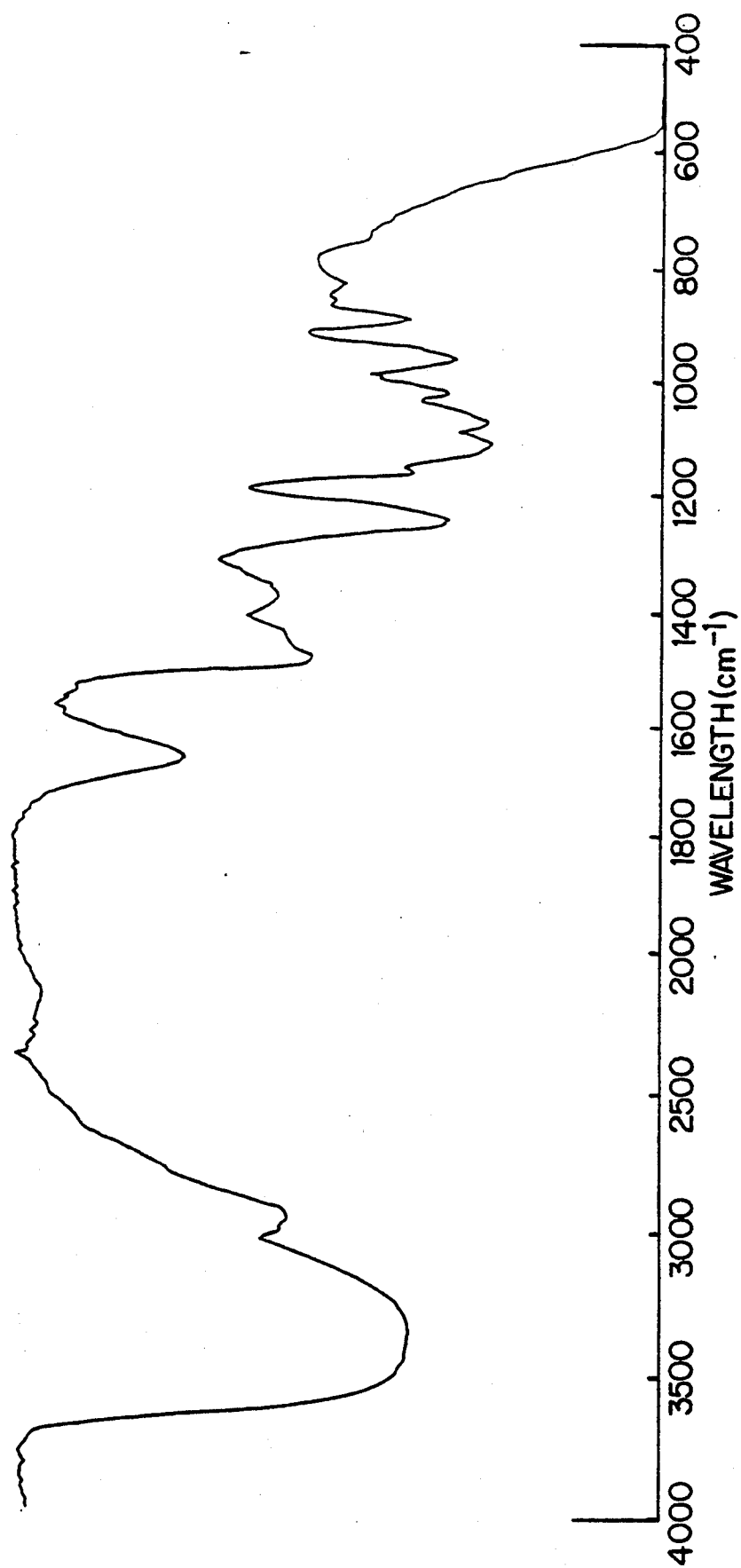
FIG. 3 is the IR spectrum of α-D-glucopyranose-1-[2-hydroxy-3-{N-(2-hydroxyethyl)-N,N-dimethylammonio}propyl]phosphate obtained in Example 13.

IR (liquid film): refer to FIG. 3.
Mass spectrometry (FAB ionization method):
M/Z406(M+H)+(M=$C_{13}H_{28}O_{11}NP$)

EXAMPLE 14

Synthesis of
α-D-glucopyranose-1-[3-{N,N-di(2-hydroxyethyl)-N-methylammonio}-2-hydroxypropyl]phosphate 105 g (0.3 mol) of α-D-glucose-1-phosphate monosodium salt and 500 g of water were introduced into a reactor and heated to 60° C. Then a solution of 191 g (0.9 mol) of glycidyldi(2-hydroxyethyl)methylammonium chloride dissolved in 200 g of water was slowly added dropwise thereto, while maintaining the reaction system at 60° C. Next, the reaction was carried out at 60° C. for 15 hours. After the completion of the reaction, the solvent was distilled off under reduced pressure and the residue thus obtained was washed with 10 times of ethanol as much as the residue by volume to thereby remove the unreacted glycidyldi(2-hydroxyethyl)methylammonium chloride and the epoxy-ring opened product thereof. The crude product thus obtained was dissolved in 200 g of water and purified by ion exchange chromatography (ion exchange resin: AG501-X8, trade name, manufactured by BIO-RAD Co.). Thus, 59 g of α-D-glucopyranose-1-[3-{N,N-di(2-hydroxyethyl)-N-methylammonio}-2-hydroxypropyl]phosphate was obtained (isolation yield: 45%).

This product was a hygroscopic, grease-like and colorless solid showing a purity of 99% when examined with HPLC (column: TSK-GEL G2500PW, trade name, manufactured by Tosoh Co.; eluent: water).

$^1$H-NMR ($D_2O$); δ (ppm):
3.21 (s, 3H, a), 3.38–3.97 (broad, m, 14H, b), 4.04 (t, 4H, c), 4.41 (broad, 1H, d), 5.45 (m, 1H, e)

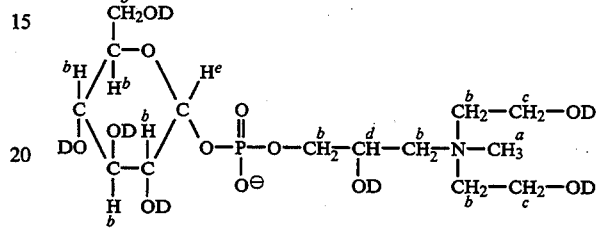

Mass spectrometry (FAB ionization method):
M/Z436(M+H)+(M=$C_{14}H_{30}O_{12}NP$)

EXAMPLE 15

Synthesis of
fructose-1,6-di[2-hydroxy-3-{N,N-dimethyl-N-(2-hydroxyethyl)ammonio}propyl]phosphate 45 g (0.09 mol) of fructose-1,6-diphosphate trisodium salt hexahydrate and 200 g of water were introduced into a reaction vessel dissolved by stirring and heated to 60° C. Then a solution of 73 g (0.4 mol) of glycidyl-2-hydroxyethyldimethylammonium chloride dissolved in 200 g of water was slowly added thereto and the reaction was carried out at 60° C. for 20 hours. After the completion of the reaction, the solvent was distilled off under reduced pressure and the residue thus obtained was washed with 10 times of ethanol as much as the residue by volume to thereby remove the unreacted glycidyl-2-hydroxyethyldimethylammonium chloride and the epoxy-ring opened product thereof. The crude product thus obtained was dissolved in 300 g of water and purified by ion exchange chromatography (ion exchange resin: AG501-X8, trade name, manufactured by BIO-RAD Co.). Thus, 18.3 g of fructose-1,6-di[2-hydroxy-3-{N,N-dimethyl-N-(2-hydroxyethyl)ammonio}propyl]phosphate was obtained (isolation yield: 32%).

$^1$H-NMR ($D_2O$); δ (ppm): 3.13 (s, 12H, a), 3.31–3.94 (broad, m, 19H, b), 4.04 (t, 4H, c), 4.35 (broad, m, 2H, d)

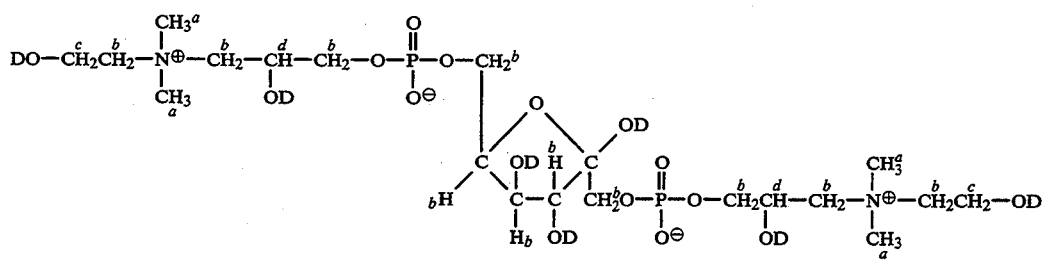

Mass spectrometry (FAB ionization method):
M/Z631(M+H)+(M=$C_{20}H_{44}O_{16}N_2P_2$)

EXAMPLE 16

Synthesis of 2,3-dihydroxypropyl[2-hydroxy-3-{N,N-dimethyl-N-(2-hydroxyethyl)ammonio}propyl]phosphate 65 g (0.3 mol) of disodium α-glycerophosphate, 250 g of water and 300 g of 1N hydrochloric acid were introduced into a reaction vessel, dissolved by stirring and heated to 60° C. Then a solution of 109 g (0.6 mol) of glycidyl-2-hydroxyethyldimethylammonium chloride dissolved in 100 g of water was slowly added thereto. Next, the reaction was carried out at 60° C. for 10 hours. After the completion of the reaction, the solvent was distilled off under reduced pressure and the residue thus obtained was washed with 5 times of ethanol as much as the residue by volume thrice to thereby remove the unreacted glycidyl-2-hydroxyethyldimethylammonium chloride and the epoxy-ring opened product thereof. The crude product thus obtained was dissolved in 200 g of water and purified by ion exchange chromatography (ion exchange resin: AG501-X8, trade name, manufactured by BIO-RAD Co.). Thus, 42 g of 2,3-dihydroxypropyl[2-hydroxy-3-{N,N-dimethyl-N-(2-hydroxyethyl)ammonio}propyl]phosphate was obtained (isolation yield: 44%).

$^1$H-NMR (D$_2$O); δ (ppm): 3.17 (s, 6H, a), 3.40–3.94 (broad, m, 11H, b), 4.03 (t, 2H, c), 4.39 (broad, 1H, d)

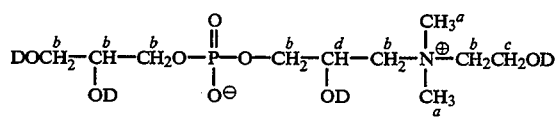

Mass spectrometry (FAB ionization method):
M/Z318(M+H)$^+$(M=C$_{10}$H$_{24}$O$_8$NP)

EXAMPLE 17

Synthesis of pentahydroxyhexyl[2-hydroxy-3-{N,N-dimethyl-N-(2-hydroxyethyl)ammonio}propyl]phosphate 83 g (0.3 mol) of sorbitolphosphate sodium salt prepared in accordance with Synthetic Example 1 above and 250 g of water were introduced into a reaction vessel, dissolved by stirring. After adjusting the pH value to 6.5 with a dilute hydrochloric acid, the solution was heated to 60° C. Then a solution of 164 g (0.9 mol) of glycidyl-2-hydroxyethyldimethylammonium chloride dissolved in 150 g of water was slowly added thereto. Next, the reaction was carried out at 60° C. for 20 hours. After the completion of the reaction, the solvent was distilled off under reduced pressure and the residue thus obtained was washed with 10 times of ethanol as much as the residue by volume thrice to thereby remove the unreacted glycidyl-2-hydroxyethyldimethylammonium chloride and the epoxy-ring opened product thereof. The crude product thus obtained was dissolved in 300 g of water and purified by ion exchange chromatography (ion exchange resin: AG501-X8, trade name, manufactured by BIO-RAD Co.). Thus, 47 g of pentahydroxyhexyl[2-hydroxy-3-{N,N-dimethyl-N-(2-hydroxyethyl)ammonio}propyl]phosphate was obtained (isolation yield: 38%).

$^1$H-NMR (D$_2$O); δ (ppm):

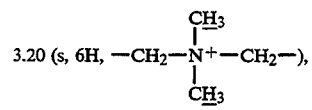

3.20 (s, 6H, —CH$_2$—N$^+$—CH$_2$—), 3,28–3.92 (broad, m, 14H, proton originating from the sorbitol residue and

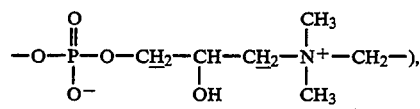

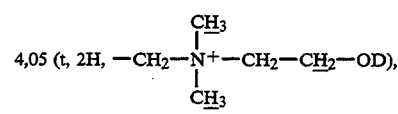

4,05 (t, 2H, —CH$_2$—N$^+$—CH$_2$—CH$_2$—OD),

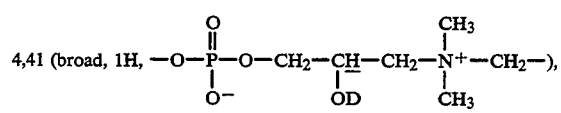

4,41 (broad, 1H, —O—P(O)(O$^-$)—O—CH$_2$—CH—CH$_2$—N$^+$—CH$_2$—),

Mass spectrometry (FAB ionization method):
M/Z408(M+H)$^+$(M=C$_{13}$H$_{30}$O$_{11}$NP)

EXAMPLE 18

Synthesis of maltose[2-hydroxy-3-{N,N-dimethyl-N-(2-hydroxyethyl)ammonio}propyl]phosphate 93 g (0.2 mol) of maltose phosphate disodium salt prepared in accordance with Synthetic Example 2 above, 400 g of water and 200 g of 1N hydrochloric acid were introduced into a reaction vessel, dissolved by stirring and heated to 60° C. Then a solution of 109 g (0.6 mol) of glycidyl-2-hydroxyethyldimethylammonium chloride dissolved in 100 g of water was slowly added thereto. Next, the reaction was carried out at 60° C. for 20 hours. After the completion of the reaction, the solvent was distilled off under reduced pressure and the residue thus obtained was washed with 10 times of ethanol as much as the residue by volume thrice to thereby remove the unreacted glycidyl-2-hydroxyethyldimethylammonium chloride and the epoxy-ring opened product thereof. The crude product thus obtained was dissolved in 300 g of water and purified by ion exchange chromatography (ion exchange resin: AG501-X8, trade name, manufactured by BIO-RAD Co.). Thus, 49 g of maltose[2-hydroxy-3-{N,N-dimethyl-N-(2-hydroxyethyl)ammonio}propyl]phosphate was obtained (isolation yield: 43%).

$^1$H-HMR (D$_2$O); δ (ppm):

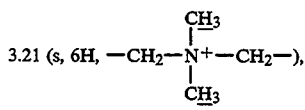

3.21 (s, 6H, —CH$_2$—N$^+$—CH$_2$—), 3,38–3.95 (broad, m, 18H, protons originating from the maltose residue, except those bonding to the anomer carbon, and

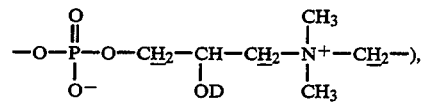

4,07 (t, 2H, —CH₂—N⁺(CH₃)₂—CH₂—CH₂—OD),

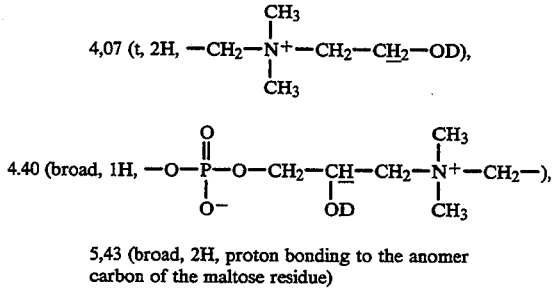

5,43 (broad, 2H, proton bonding to the anomer carbon of the maltose residue)

Mass spectrometry (FAB ionization method):
M/Z 568(M+H)⁺ (M=C₁₉H₃₈O₁₆NP)

SYNTHETIC EXAMPLE 3

Synthesis of Maltitol Phosphate

Maltitol phosphate sodium salt was prepared by a conventional method (refer to JP-B-50-8052).

Namely, the procedure of the above Synthetic Example 1 was repeated except that 50 g of maltitol was dissolved in 200 ml of water. Thus 45 g of purified maltitol phosphate disodium salt was obtained.

EXAMPLE 19

Synthesis of 2,3,4,5,6-pentahydroxyhexyl-{(2-hydroxy-3-N,N,N-trimethyl- ammonio)propyl}phosphate 89 g (0.32 mol) of sorbitol phosphate sodium salt prepared in accordance with Synthetic Example 1 and 500 g of water were introduced into a reaction vessel and, after adjusting pH to 6.5 with a dilute hydrochloric acid, heated to 60° C. Then a solution of 150 g (0.99 mol) of glycidyltrimethylammonium chloride dissolved in 500 g of ion exchanged water was added dropwise thereto over 3 hours, while maintaining the reaction system at 60° C. Next, the reaction was carried out at 60° C. for 15 hours. After the completion of the reaction, the solvent was distilled off under reduced pressure and the residue was washed 10 times of ethanol as much as the residue by volume to thereby remove the unreacted glycidyltrimethylammonium chloride and the epoxy-ring opened product thereof. The crude product thus obtained was purified by ion exchange chromatography (ion exchange resin: AG501X8, trade name, manufactured by BIO RAD Co.). Thus 71.2 g of 2,3,4,5,6-pentahydroxyhexyl-{(2-hydroxy-3-N,N,N-trimethylammonio)propyl}phosphate was obtained (isolation yield: 59%).

Figure 4:
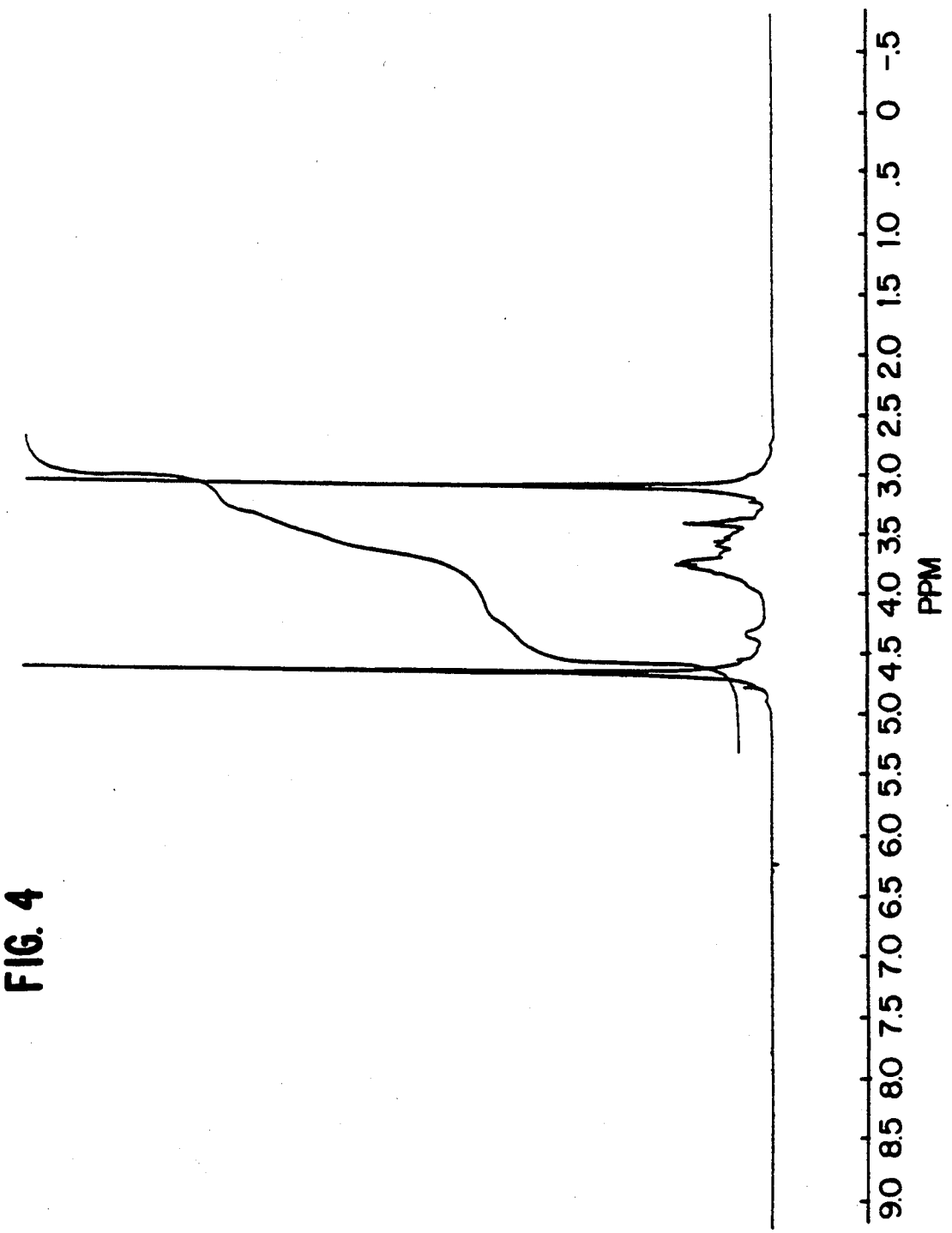
FIG. 4 is the $^1$H-NMR spectrum of 2,3,4,5,6-pentahydroxyhexyl-(2-hydroxy-3-N,N,N-trimethylammoniopropyl)phosphate obtained in Example 19.

¹H-NMR (D₂O): refer to FIG. 4. δ (ppm): 3.12 (s, 9H, a), 3.28–4.05 (m, 12H, b), 4.33 (broad, 1H, c)

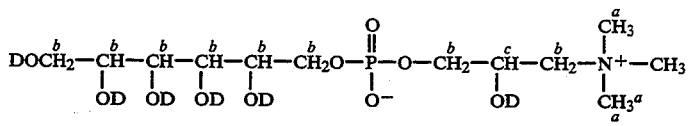

Mass spectrometry (FAB ionization method):
M/Z 378(M+H)⁺ (M=C₁₂H₂₈O₁₀NP)

EXAMPLE 20

Synthesis of 2,3-dihydroxypropyl-{(2-hydroxy-3-N,N,N-trimethylammonio)propyl}phosphate 50 g (0.23 mol) of disodium α-glycerophosphate, 500 g of water and 230 g of 1N hydrochloric acid were introduced into a reaction vessel and heated to 60° C. Then a solution of 106 g (0.70 mol) of glycidyltrimethylammonium chloride dissolved in 500 g of ion exchanged water was added dropwise thereto over 5 hours, while maintaining the reaction system at 60° C. Next, the reaction was carried out at 60° C. for 15 hours. After the completion of the reaction, the solvent was distilled off under reduced pressure and the residue was washed 10 times of ethanol as much as the residue to thereby remove the unreacted glycidyltrimethylammonium chloride and the epoxy-ring opened product thereof. The crude product thus obtained was purified by ion exchange chromatography (ion exchange resin: AG501X8, trade name, manufactured by BIO-RAD Co.). Thus 31 g of 2,3-dihydroxypropyl-{(2-hydroxy-3-N,N,N-trimethylammonio)propyl}phosphate was obtained (isolation yield: 38%).

¹H-HMR (D₂O): δ (ppm): 3.18 (s, 9H, a), 3.29–3.94 (m, 9H, b), 4.33 (broad, 1H, c)

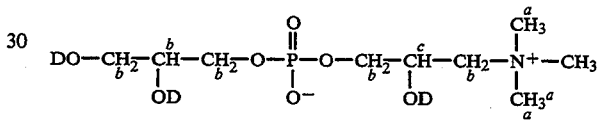

Mass spectrometry (FAB ionization method):
M/Z 360(M+H)⁺ (M=C₁₅H₂₂O₇NP)

EXAMPLE 21

Synthesis of maltose-{(2-hydroxy-3-N,N,N-trimethylammonio)-propyl}phosphate 93 g (0.2 mol) of maltosephosphate disodium salt prepared in accordance with Synthetic Example 2, 500 g of water and 200 g of 1N hydrochloric acid were introduced into a reaction vessel and heated to 60° C. Then a solution of 106 g (0.70 mol) of glycidyltrimethylammonium chloride dissolved in 500 g of ion exchanged water was added dropwise thereto over 5 hours, while maintaining the reaction system at 60° C. Next, the reaction was carried out at 60° C. for 15 hours. After the completion of the reaction, the solvent was distilled off under reduced pressure and the residue was washed 10 times of ethanol as much as the residue by volume to thereby remove the unreacted glycidyltrimethylammonium chloride and the epoxy-ring opened product thereof. The crude product thus obtained was purified by ion exchange chromatography (ion exchange resin: AG501X8, trade name, manufactured by BIO-RAD Co.). Thus 55 g of maltose-{(2-hydroxy-3-

N,N,N-trimethylammonio)propyl}phosphate was obtained (isolation yield: 51%).

1H-NMR (D2O): δ (ppm):

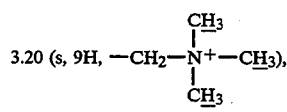

3.20 (s, 9H, —CH2—N+—CH3), 3,38–3.98 (broad, m, 16H, protons originating from the maltose residue, except those bonding to anomer carbon, and

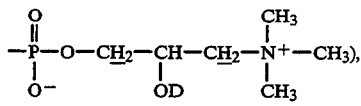

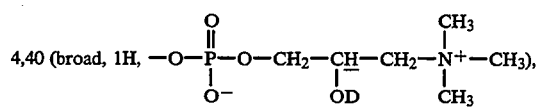

4,40 (broad, 1H, —O—P(=O)(O−)—O—CH2—CH(OD)—CH2—N+(CH3)3), 5.43 (broad, 2H, protons bonding to the anomer carbon of the maltose residue)

Mass spectrometry (FAB ionization method):
M/Z538(M+H)+(M=C18H36O15NP)

EXAMPLE 22

Synthesis of maltitol-{(2-hydroxy-3-N,N,N-trimethylammonio)-propyl}phosphate 47 g (0.11 mol) of maltitolphosphate sodium salt prepared in accordance with Synthetic Example 3 and 500 g of water were introduced into a reaction vessel and, after adjusting the pH value to 6.5 with a dilute hydrochloric acid, heated to 60° C. Then a solution of 61 g (0.16 mol) of glycidyltrimethylammonium chloride dissolved in 200 g of ion exchanged water was added dropwise thereto over 3 hours, while maintaining the reaction system at 60° C. Next, the reaction was carried out at 60° C. for 15 hours. After the completion of the reaction, the solvent was distilled off under reduced pressure and the residue was washed 6 times of ethanol as much as the residue by volume to thereby remove the unreacted glycidyltrimethylammonium chloride and the epoxy-ring opened product thereof. The crude product thus obtained was purified by ion exchange chromatography (ion exchange resin: AG501X8, trade name, manufactured by BIO-RAD Co.). Thus 19.6 g of maltitol-{(2-hydroxy-3-N,N,N-trimethylammonio)-propyl}phosphate was obtained (isolation yield: 33%).

1H-NMR (D2O): δ (ppm):

3.15 (s, 9H, —CH2—N+(CH3)—CH3), 3.25–4.10 (broad, m, 18H, protons originating from the maltitol residue, except those bonding to the anomer carbon, and

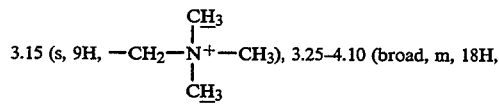

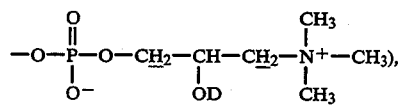

4,35 (broad, 1H, —O—P(=O)(O−)—O—CH2—CH(OD)—CH2—N+(CH3)3), 5.05 (broad, 2H, protons bonding to the anomer carbon of the maltitol residue)

Mass spectrometry (FAB ionization method):
M/Z540 (M+H)+(M=C18H38O15NP)

EXAMPLE 23

Synthesis of poly[3-(N,N,N-trimethylammonio)-2-hydroxypropyl-phosphate] of starch 2 l of water was introduced into a reaction vessel and heated to 60° C. under stirring. Then 50 g of starch phosphate (degree of phosphorylation=0.06 mol phosphate/glucose unit) was slowly added thereto and dissolved. Next, 17.0 g (0.11 mol; 7 times by mol as much as the phosphate group of the starch phosphate) of glycidyltrimethylammonium chloride was added thereto, while maintaining the reaction system at 60° C. Then the reaction was carried out at 60° C. for 15 hours. After the completion of the reaction, the reaction mixture was cooled to room temperature and 2 l of ethanol was added to thereby precipitate the reaction product. The crude product thus obtained was redissolved in 1.6 l of water. Then 2 l of ethanol was added thereto to thereby reprecipitate the reaction product. The precipitate thus obtained was washed with a small amount of ethanol several times and then dried under reduced pressure. Thus 27 g of poly[3-(N,N,N-trimethylammonio)-2-hydroxypropylphosphate] of starch was obtained. The 1H-NMR spectrum of this compound indicated that one 3-(N,N,N-trimethylammonio)-2-hydroxypropylphosphate group bonded per about 15 glucose residues in this compound.

Figure 5:
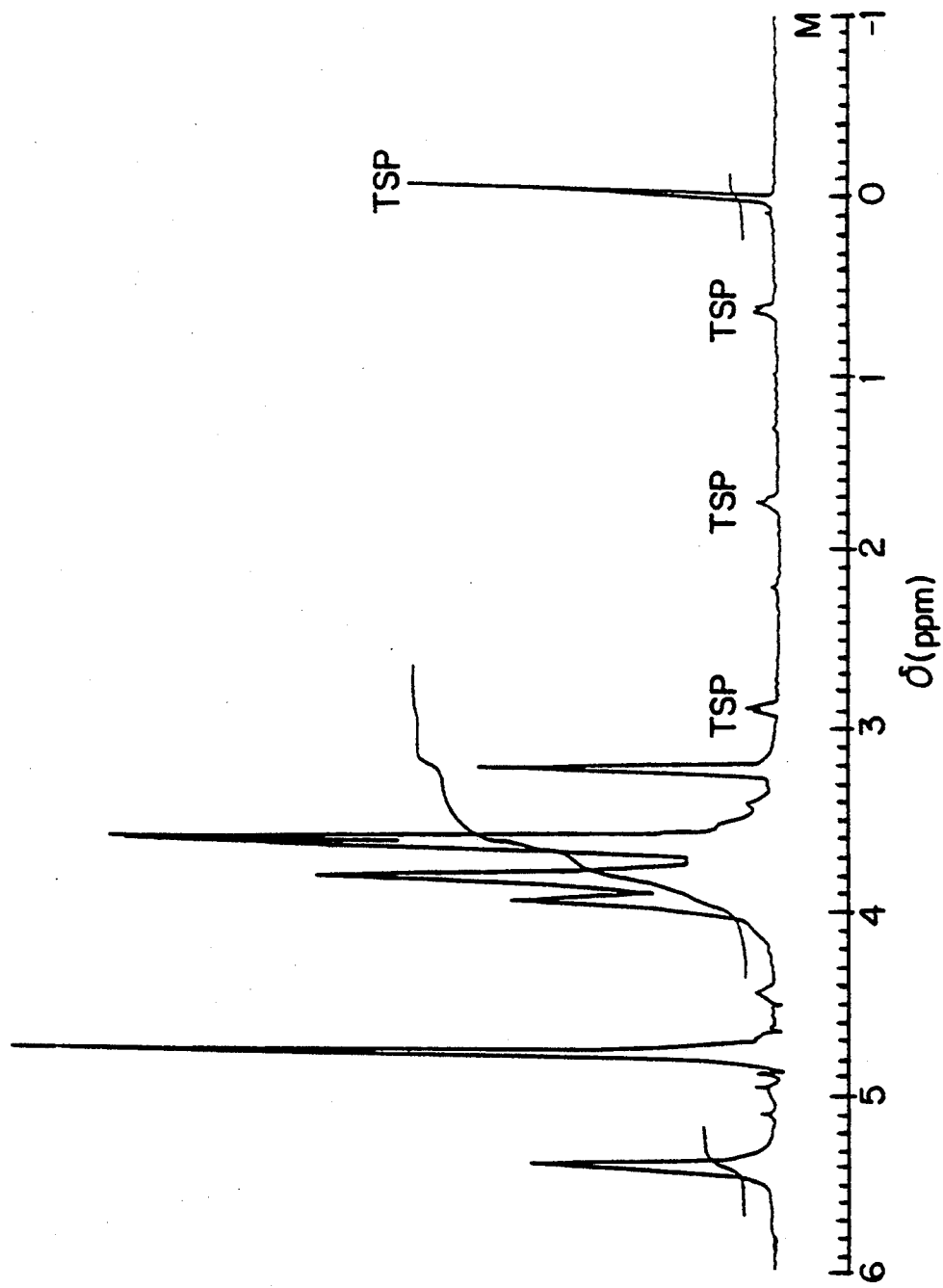
FIG. 5 is the $^1$H-NMR spectrum of starch poly[3-(N,N,N-trimethylammonio)-2-hyrdoxypropylphosphate] obtained in Example 23.

1H-NMR (D2O): refer to FIG. 5.; δ (ppm) (TSP standard):

3.24 (s, 9H, —N(CH3)3), 3.35–4.20 (broad, m, 94H, protons originating from the glucose residue and

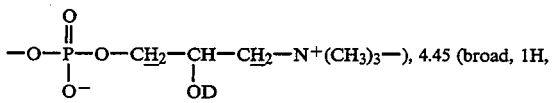

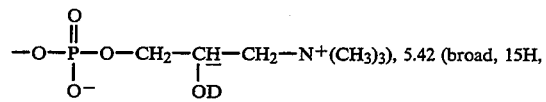

the glucose residue anomer protons)

Figure 6:
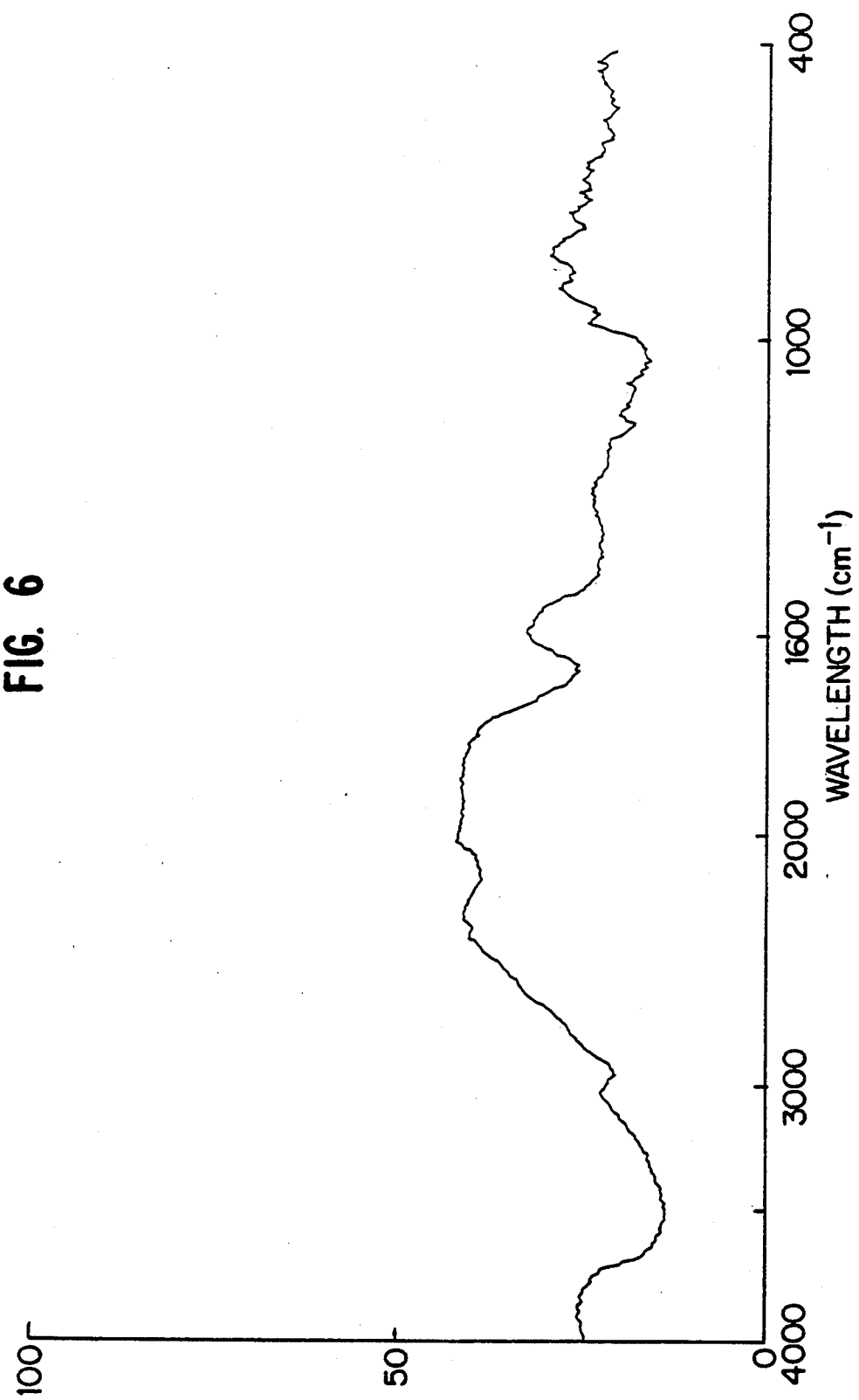
FIG. 6 is the IR spectrum of starch poly[3-(N,N,N-trimethylammonio)-2-hyrdoxypropylphosphate] obtained in Example 23.

IR (KBr pellet method): refer to FIG. 6
Elemental analysis: P: 1.0% (calculated: 1.0%) N: 0.46% (calculated: 0.45%).

EXAMPLE 24

Synthesis of poly[3-(N,N,N-trimethylammonio)-2-hydroxypropyl-phosphate] of starch phosphate 2 l of water was introduced into a reaction vessel and heated to 60° C. under stirring. Then 50 g of starch phosphate (degree of phosphorylation=0.10 mol phosphate/glucose unit) was slowly added thereto and dissolved. Next, 2.2 g (0.014 mol; 0.5 time by mol as much as the phosphate group of the starch phosphate) of glycidyltrimethylammonium chloride was added thereto, while maintaining the reaction system at 60° C. Then the reaction was carried out at 60° C. for 15 hours. After the completion of the reaction, the reaction mixture was cooled to room temperature and 2 l of ethanol was added to thereby precipitate the reaction product. The crude product thus obtained was redissolved in 1.6 l of water. Then 2 l of ethanol was added thereto to thereby reprecipitate the reaction product. The precipitate thus obtained was washed with a small amount of ethanol several times and then dried under reduced pressure. Thus 21 g of poly[3-(N,N,N-trimethylammonio)-2-hydroxypropylphosphate] of starch phosphate was obtained. The $^1$H-NMR spectrum of this compound indicated that one 3-(N,N,N-trimethylammonio)-2-hydroxypropylphosphate group and three phosphate groups bonded per about 30 glucose residues in this compound.

$^1$H-NMR (D$_2$O): δ (ppm) (TSP standard):

3.25 (s, 9H, —N$^+$(CH$_3$)$_3$), 3.31–4.21 (broad, m, 180H, protons originating from the glucose residue and

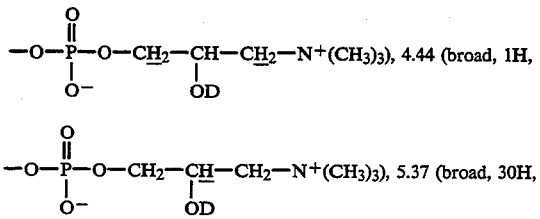

, 4.44 (broad, 1H,

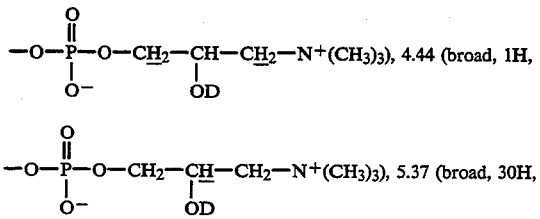

, 5.37 (broad, 30H, the glucose residue anomer protons)

Elemental analysis: P: 1.7% (calculated: 1.7%) N: 0.19% (calculated: 0.19%)

EXAMPLE 25

Synthesis of poly[3-(N-dodecyl-N,N-dimethylammonio)-2-hydroxypropylphosphate] of starch 2 l of water was introduced into a reaction vessel and heated to 60° C. under stirring. Then 50 g of starch phosphate (degree of phosphorylation=0.1 mol phosphate/glucose unit) was slowly added thereto and dissolved. Next, a solution of 31.3 g (0.13 mol; 5 time by mol as much as the phosphate group of the starch phosphate) of glycidyldimethyldodecylammonium chloride dissolved in 200 ml of water was slowly added dropwise thereto, while maintaining the reaction system at 60° C. Then the reaction was carried out at 60° C. for 15 hours. After the completion of the reaction, the reaction mixture was concentrated by distilling off the solvent under reduced pressure and then further lyophilized. The obtained residue was washed with 500 ml of acetone thrice and then dissolved in 1.5 l of water. 1.5 l of acetone was added to thereby precipitate the reaction product. The obtained precipitate was washed with a small amount of acetone and then dried under reduced pressure. Thus 21 g of poly[3-(N-dodecyl-N,N-dimethylammonio)-2-hydroxypropylphosphate] of starch was obtained. The $^1$H-NMR spectrum of this compound indicated that one 3-(N-dodecyl-N,N-dimethylammonio)-2-hydroxypropylphosphate group bonded per about 10 glucose residues in this compound.

$^1$H-NMR (D$_2$O): δ (ppm) (TSP standard):

0.87 (t, 3H, —CH$_2$—C$\underline{H}$$_3$), 1.31 (broad, 18H,

—CH$_2$—(C$\underline{H}$$_2$)$_9$—CH$_3$), 1.75 (broad, 2H,

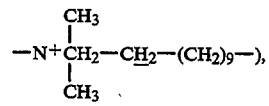

), 3.20 (s, 6H, 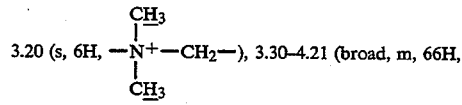, 3.30–4.21 (broad, m, 66H, protons originating from the glucose residues and

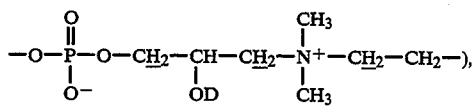, 4.41 (broad, 1H, 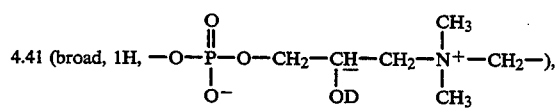, 5.44 (broad, 10H, the glucose residue anomer protons)

Elemental analysis: P: 1.7% (calculated: 1.7%) N: 0.78% (calculated: 0.77%)

EXAMPLE 26

Synthesis of poly[2-hydroxy-3-{N-(2-hydroxyethyl)-N,N-dimethylammonio}propyl]phosphate of starch 2 l of water was introduced into a reaction vessel and heated to 60° C. under stirring. Then 50 g of starch phosphate (degree of phosphorylation=0.06 mol phosphate/glucose unit) was slowly added thereto and dissolved. Next, 20.0 g (0.11 mol; 7 times by mol as much as the phosphate group of the starch phosphate) of glycidyl- (2-hydroxyethyl)-dimethylammonium chloride was added thereto, while maintaining the reaction system at 60° C. Then the reaction was carried out at 60° C. for 15 hours. After the completion of the reaction, the reaction mixture was cooled to room temperature and 2 l of ethanol was added to thereby precipitate the reaction product. The crude product thus obtained was redissolved in 1.6 l of water. Then 2 l of ethanol was added thereto to thereby reprecipitate the reaction product. The precipitate thus obtained was washed with a small amount of ethanol several times and then dried under reduced pressure. Thus 32 g of poly[2-hydroxy-3-{N-(2-hydroxyethyl)-N,N-dimethylammonio}propyl]phosphate of starch was obtained. The $^1$H-NMR spectrum of this compound indicated that one [2-hydroxy-3-{N-(2-hydroxyethyl)-N,N-dimethylammonio}propyl]phosphate group bonded per about 16 glucose residues in this compound.

$^1$H-NMR (D$_2$O): δ (ppm) (TSP standard):

3.22 (s, 6H, 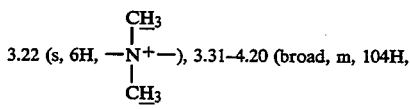), 3.31–4.20 (broad, m, 104H, protons originating from the glucose residue and -continued

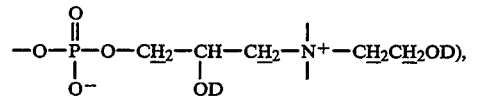

4.44 (broad, 1H, 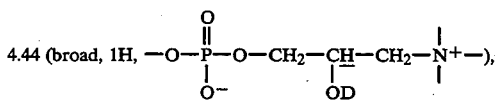), 5.42 (broad, 16H, the glucose residue anomer protons)

Elemental analysis: P: 1.0% (calculated: 1.0%) N: 0.44% (calculated: 0.45%)

EXAMPLE 27

Synthesis of poly[2-hydroxy-3-{N,N-di(2-hydroxyethyl)-N-methylammonio}propyl]phosphate of starch 2 l of water was introduced into a reaction vessel and heated to 60° C. under stirring. Then 50 g of starch phosphate (degree of phosphorylation=0.06 mol phosphate/glucose unit) was slowly added thereto and dissolved. Next, 23.3 g (0.11 mol; 7 times by mol as much as the phosphate group of the starch phosphate) of glycidyl-di(2-hydroxyethyl)methylammonium chloride was added thereto, while maintaining the reaction system at 60° C. Then the reaction was carried out at 60° C. for 15 hours. After the completion of the reaction, the reaction mixture was cooled to room temperature and 2 l of ethanol was added to thereby precipitate the reaction product. The crude product thus obtained was redissolved in 1.6 l of water. Then 2 l of ethanol was added to thereby reprecipitate the reaction product. The precipitate thus obtained was washed with a small amount of ethanol several times and then dried under reduced pressure. Thus 25 g of poly[2-hydroxy-3-{N,N-di(2-hydroxyethyl)-N-methylammonio}propyl]phosphate of starch was obtained. The $^1$H-NMR spectrum of this compound indicated that one [2-hydroxy-3-{N,N-di(2-hydroxyethyl)-N-methylammonio}propyl]phosphate group bonded per about 15 glucose residues in this compound.

$^1$H-NMR (D$_2$O): δ (ppm) (TSP standard):

3.26 (s, 3H, 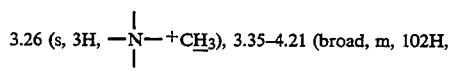), 3.35–4.21 (broad, m, 102H, protons originating from the glucose residue and

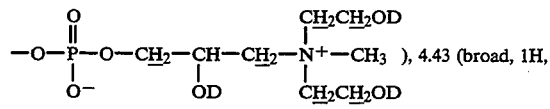, 4.43 (broad, 1H,

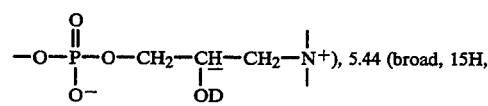, 5.44 (broad, 15H, the glucose residue anomer proton)

Elemental analysis: P: 1.0% (calculated: 1.0%) N: 0.45% (calculated: 0.45%).

EXAMPLE 28

Synthesis of poly[2-hydroxy-3-{N-(2-hydroxyethyl)-N,N-dimethylammonio}propyl]phosphate of starch phosphate 2 l of water was introduced into a reaction vessel and heated to 60° C. under stirring. Then 50 g of starch phosphate (degree of phosphorylation=0.10 mol phosphate/glucose unit) was slowly added thereto and dissolved. Next, 2.5 g (0.014 mol; 0.5 time by mol as much as the phosphate group of starch phosphate) of glycidyl-(2-hydroxyethyl)dimethylammonium chloride was added thereto, while maintaining the reaction system at 60° C. Then the reaction was carried out at 60° C. for 15 hours. After the completion of the reaction, the reaction mixture was cooled to room temperature and 2 l of ethanol was added to thereby precipitate the reaction product. The crude product thus obtained was redissolved in 1.6 l of water. Then 2 l of ethanol was added thereto to thereby reprecipitate the reaction product. The precipitate thus obtained was washed with a small amount of ethanol several times and then dried under reduced pressure. Thus 29 g of poly[2-hydroxy-3-{N-(2-hydroxyethyl)-N,N-dimethylammonio}propyl]phosphate of starch phosphate was obtained. The $^1$H-NMR spectrum of this compound indicated that one [2-hydroxy-3-{N-(2-hydroxyethyl)-N,N-dimethylammonio}propyl]phosphate group and three phosphate groups bonded per about 30 glucose residues in this compound.

$^1$H-NMR (D$_2$O): δ (ppm) (TSP standard):

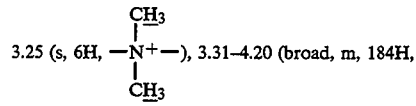, 3.31–4.20 (broad, m, 184H, protons originating from the glucose residue and

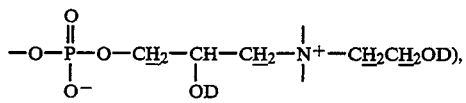, 4.42 (broad, 1H, 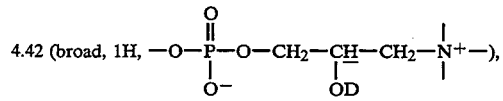), 5.40 (broad, 30H, the glucose anomer proton)

Elemental analysis: P: 1.7% (calculated: 1.7%) N: 0.18% (calculated: 0.19%).

SYNTHETIC EXAMPLE 4

Synthesis of Polyglycerol Phosphate Sodium Salt 115.5 g of polyglycerol (average degree of condensation=6) was dissolved in 460 ml of water. Then 38.4 g of phosphorus oxychloride was added dropwise thereto over about 2 hours under stirring at 0° to 5° C. During this period, a 10N aqueous solution of caustic soda was added to the reaction mixture so as to continuously maintain the pH value of the mixture at 13.5. After the completion of the addition of the phosphorus oxychloride, the addition of the caustic soda was further continued until no change in pH value was observed any more. Then the reaction mixture was neutralized with the use of a cation exchange resin (Dowex 50X4H+ type, trade name, manufactured by Dow Chemical Co.) and concentrated under reduced pressure. Next, the pH value thereof was adjusted to 10 by adding an aqueous solution of caustic soda. Then 120 ml of ethanol was added and the mixture was cooled, followed by removing the inorganic salt thus precipitated by filtering. The filtrate separated into two phases and the lower one was collected. The total volume thereof was adjusted to 250 ml by adding water and 1 l of methanol was further added thereto. The polyglycerol phosphate sodium salt thus precipitated was filtered and dried. This crude product was dissolved in 100 ml of water again and reprecipitated by adding ethanol. Thus 95 g of purified polyglycerol phosphate sodium salt was obtained.

SYNTHETIC EXAMPLE 5

Synthesis of Polyethyleneglycol Phosphate Sodium Salt 80 g (0.2 mol) of polyethyleneglycol (average molecular weight=400) and 94 g (1.0 mol) of 104% phosphoric acid was introduced into a reaction vessel and stirred at 70° C. for 20 hours. After allowing to cool to room temperature, 25 g of water was added thereto and the mixture was heated to 60° C. and stirred for 10 hours. After cooling to room temperature, 350 g of water was added. Then a solution of 177 g (0.87 mol) of magnesium chloride dissolved in 200 g of water was added under ice-cooling. Further, 22% aqueous ammonia was added thereto until the pH value of the reaction system reached 8. The white salt thus formed was filtered and the filtrate was treated with a cation exchange resin (Dowex 50W-X8, trade name, manufactured by Dow Chemical Co.) until the pH value reached 5.0.

The amount of monophosphate was 0.2 mol when it was measured with a potentiometer (AT-118, trade name, manufactured by Kyoto Denshi K. K.). Then 27 g (0.2 mol) of 30% caustic soda was added and the solvent was distilled off under reduced pressure. Thus 83.1 g of polyethyleneglycol phosphate sodium salt was obtained as a white solid.

Figure 7:
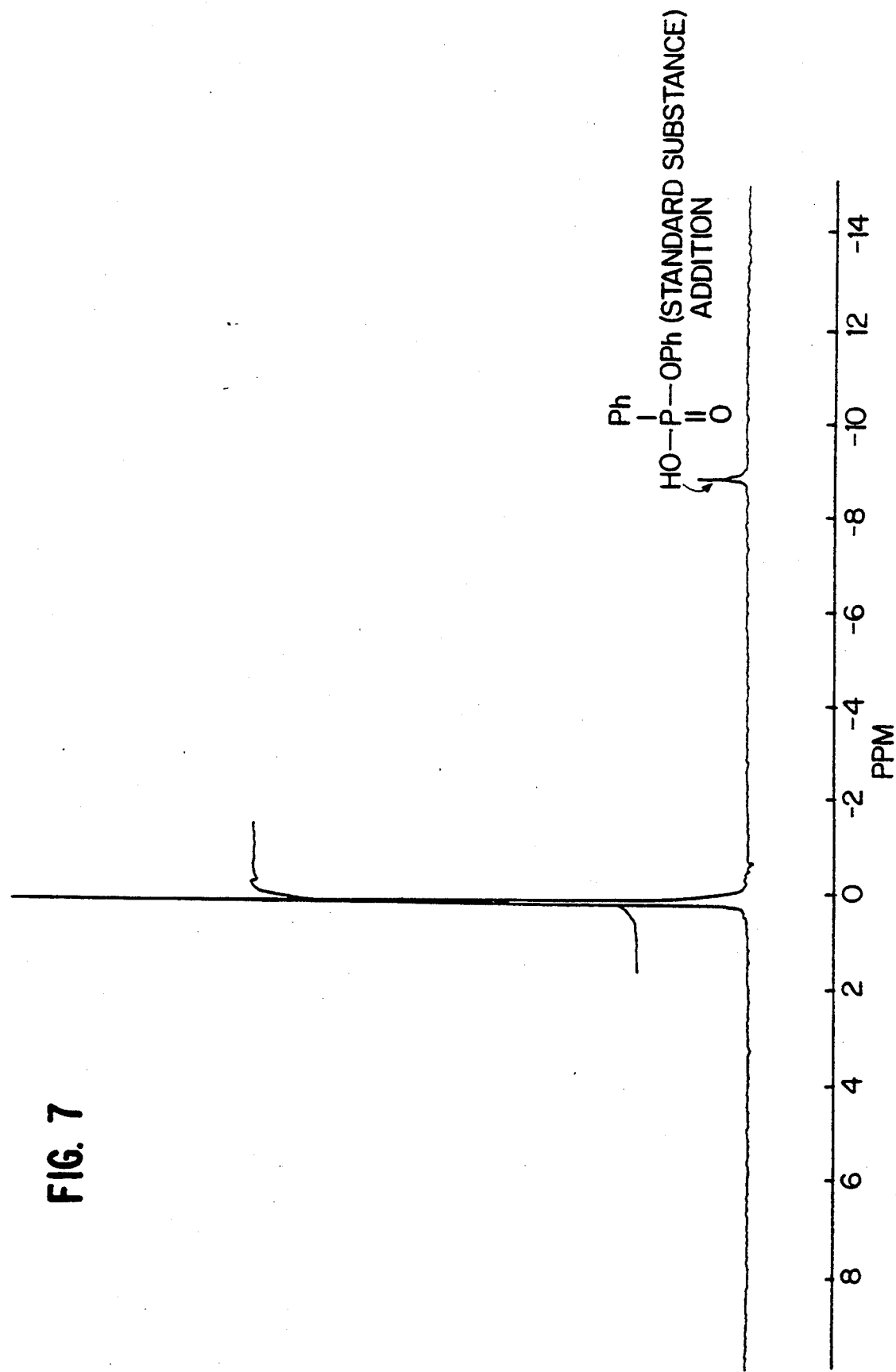
FIG. 7 is the $^{31}$P-NMR (decoupling) spectrum of polyethyleneglycol phosphate sodium salt obtained in Synthetic Example 5.

Hu 31 P-NMR (D$_2$O with 1% HCl) Standard: diphenyl phosphate (−8.8 ppm);

(Fig. 7: decoupling)   δ (ppm) 0.24 (s, —CH$_2$CH$_2$O—P(=O)(OH)—OH)

Figure 8:
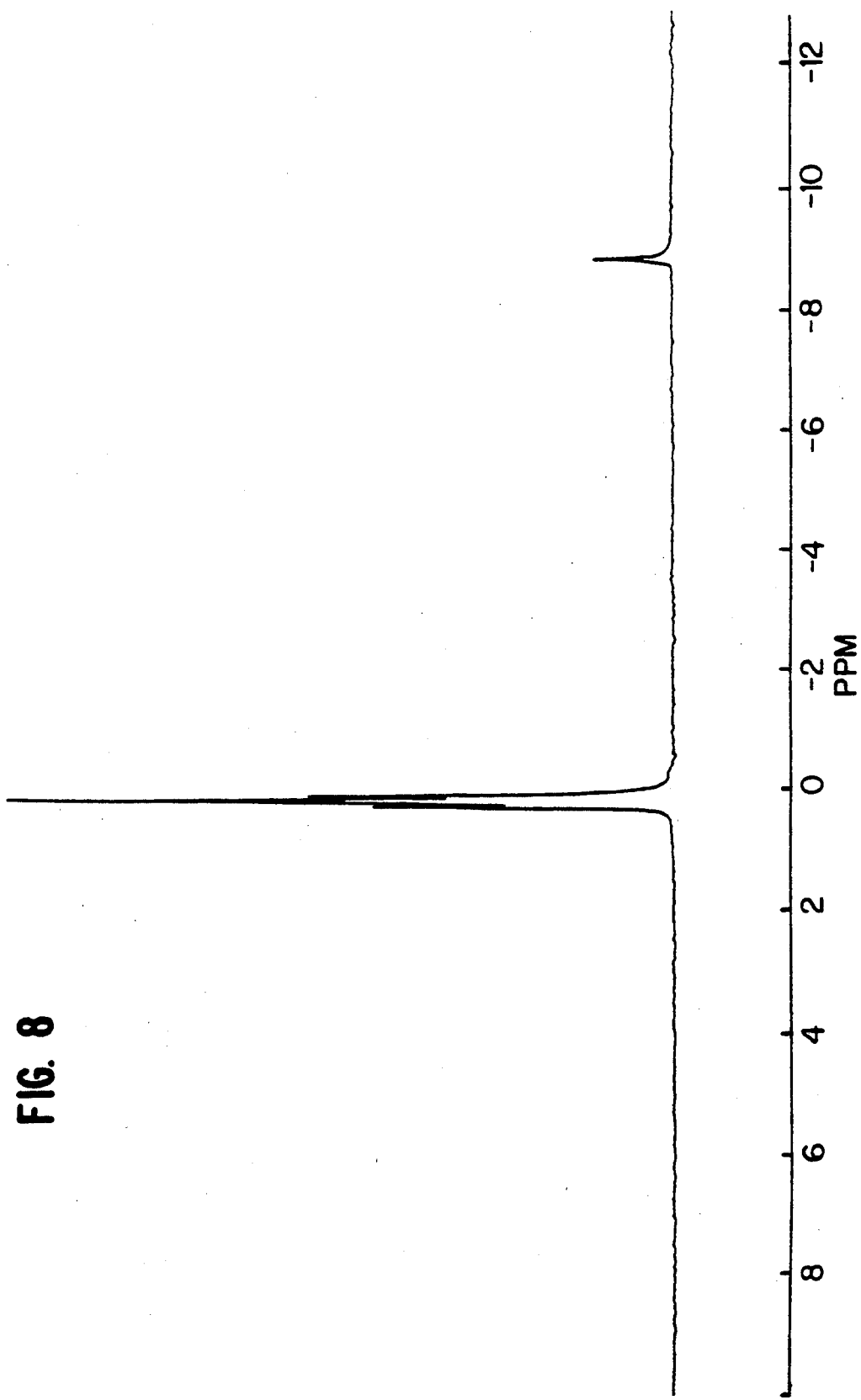
FIG. 8 is the $^{31}$P-NMR (non-decoupling) spectrum of polyethyleneglycol phosphate sodium salt obtained in Synthetic Example 5.

(Fig. 8: non-decoupling)   δ (ppm) 0.27 (t, —CH$_2$CH$_2$O—P(=O)(OH)—OH)

Mass spectrometry (FAB ionization method):
M/Z517(M+H)+(M=C$_{18}$H$_{38}$O$_{13}$PNa)

EXAMPLE 29

Synthesis of polyglycerol-(2-hydroxy-3-N,N,N-trimethylammoniopropyl)phosphate 28.2 g (0.050 mol) of polyglycerol (average degree of condensation=6) phosphate sodium salt prepared in accordance with Synthetic Example 4 and 300 g of water were introduced into a reaction vessel and heated to 60° C. Then a solution of 18 g (0.12 mol) of glycidyltrimethylammonium chloride dissolved in 50 g of ion exchanged water was added dropwise thereto over 1 hour, while maintaining the reaction system at 60° C. Next, the reaction was carried out at 60° C. for 20 hours. After the completion of the reaction, the solvent was distilled off under reduced pressure. The crude product thus obtained was purified by ion exchange chromatography (ion exchange resin: AG501X8, trade name, manufactured by BIO-RAD Co.). Thus 14.73 g of polyglycerol-(2-hydroxy-3-N,N,N-trimethylammoniopropyl)phosphate was obtained (isolation yield: 45%).

Figure 9:
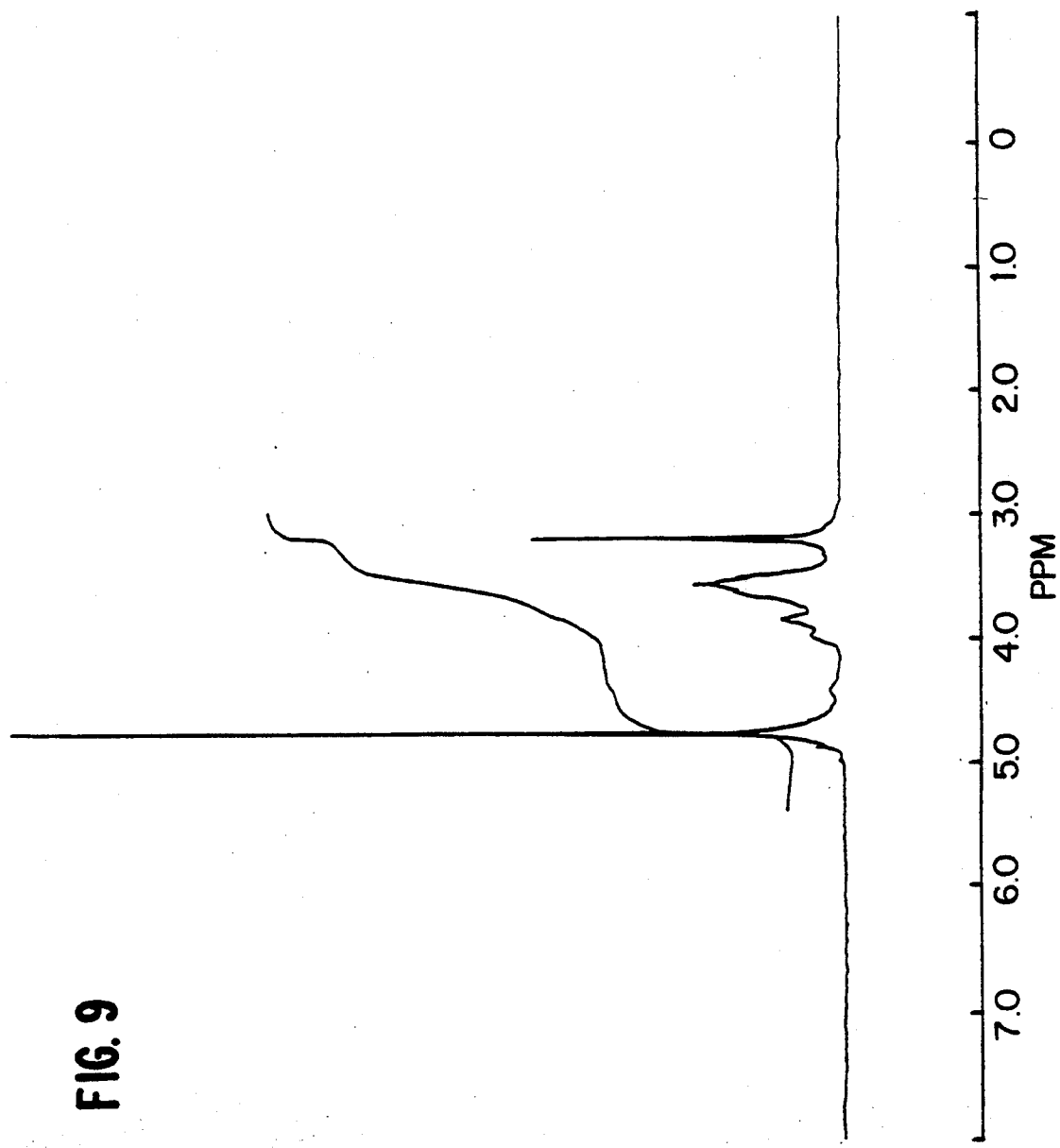
FIG. 9 is the $^1$H-NMR spectrum of polyglycerol-(2-hydroxy-3-N,N,N-trimethylammoniopropyl)phosphate obtained in Example 29.

$^1$H-NMR (D$_2$O): refer to FIG. 9; δ (ppm):
3.14 (s, 9H, a), 4.39 (broad, 1H, c), 3.34–4.04 (m, 34H, b)

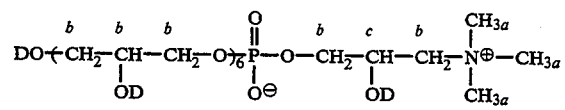

EXAMPLE 30

Synthesis of polyglycerol-{2-hydroxy-3-(N-dodecyl-N,N-dimethyl-)ammoniopropyl}phosphate 42.3 g (0.075 mol) of polyglycerol (average degree of condensation=6) phosphate sodium salt prepared in accordance with Synthetic Example 4 and 400 g of water were introduced into a reaction vessel and heated to 60° C. Then a solution of 27 g (0.18 mol) of glycidyldimethyllaurylammonium chloride dissolved in 75 g of ion exchanged water was added dropwise thereto over 1 hour, while maintaining the reaction system at 60° C. Next, the reaction was carried out at 60° C. for 20 hours. After the completion of the reaction, the solvent was distilled off under reduced pressure. The crude product thus obtained was purified by ion exchange chromatography (ion exchange resin: AG501X8, manufactured by BIO-RAD Co.). Thus 33.5 g of polyglycerol-{2-hydroxy-3-(N-dodecyl-N,N-dimethyl)ammoniopropyl} phosphate was obtained (isolation yield: 55%).

$^1$H-NMR (D$_2$O): δ (ppm): 0.86 (t, 3H, a), 1.29 (b, 18H, b), 1.75 (b, 2H, c), 3.27–4.09 (broad, m, 36H, d), 3.12 (s, 6H, e), 4.38 (b, 1H, f)

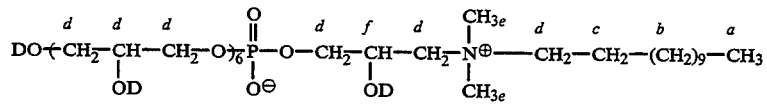

EXAMPLE 31

Synthesis of polyethyleneglycol-(2-hydroxy-3-N,N,N-trimethylammonioproypl)phosphate 52.3 g (phosphate group: 0.12 mol) of polyethyleneglycol phosphate sodium salt prepared in accordance with Synthetic Example 5 and 400 g of water were introduced into a reaction vessel and heated to 60° C. Then a solution of 36 g (0.24 mol) of glycidyltrimethylammonium chloride dissolved in 200 g of water was added dropwise thereto over 2 hours, while maintaining the reaction system at 60° C. Next, the reaction was carried out at 60° C. for 15 hours and then it was confirmed with the use of a potentiometer (AT-118, manufactured by Kyoto Denshi K. K.) that no monophosphate remained any more. After the completion of the reaction, the solvent was distilled off under reduced pressure and the solution was concentrated to 400 ml. This solution was purified by ion exchange chromatography (ion exchange resin: AG501X8, manufactured by BIO-RAD Co.) and the solvent was removed by lyophilizing. Thus 26.5 g of pure polyethyleneglycol-(2-hydroxy-3-N,N,N-trimethylammonioproypl)phosphate was obtained in the form of a white powder (isolation yield: 41.7%).

Figure 10:
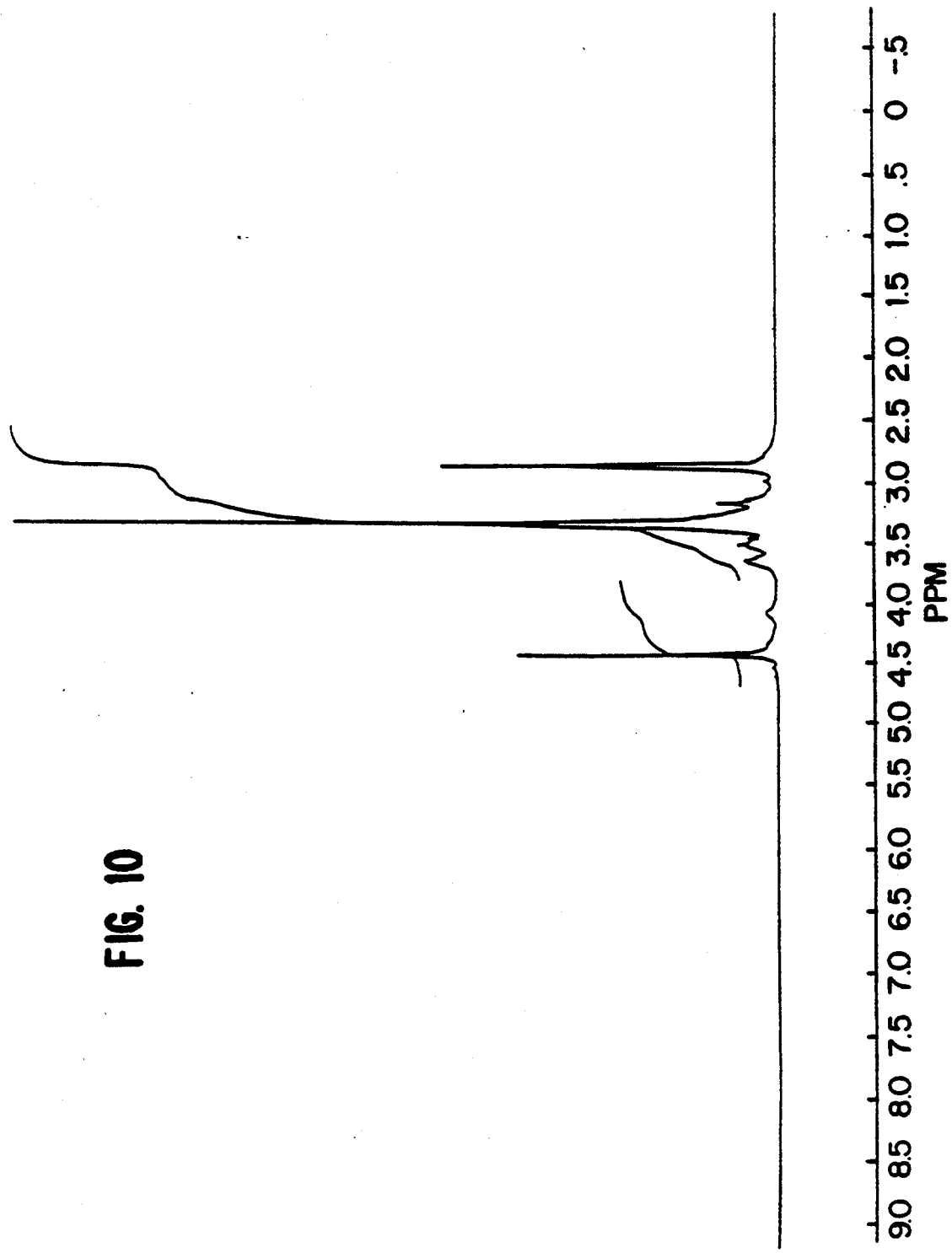
FIG. 10 is the $^1$H-NMR spectrum of polyethyleneglycol(2-hydroxy-3-N,N,N-trimethylammoniopropyl)phosphate obtained in Example 31.

$^1$H-NMR (D$_2$O): refer to FIG. 10; δ (ppm):

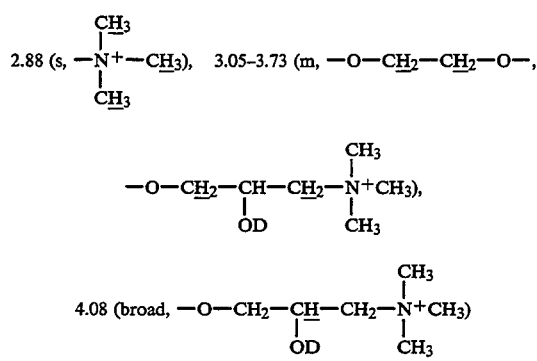

Mass spectrometry (FAB ionization method):

M/Z609(M+H)$^+$(M=C$_{24}$H$_{51}$O$_{14}$NP).

EXAMPLE 32

Synthesis of polyethyleneglycol-{2-hydroxy-3-(N-dodecyl-N,N-dimethyl)ammoniopropyl}phosphate 52.3 g (phosphate group: 6.12 mol) of polyethyleneglycol phosphate sodium salt prepared in accordance with Synthetic Example 5 and 400 g of water were introduced into a reaction vessel and heated to 60° C. Then a solution of 87.8 g (0.24 mol) of glycidyldimethyldodecylammonium chloride dissolved in 200 g of a 30% aqueous solution of ethanol was added dropwise thereto over 3 hours, while maintaining the reaction system at 60° C. Next, the reaction was carried out at 60° C. for 20 hours and then it was confirmed with the use of a potentiometer (AT-118, manufactured by Kyoto Denshi K. K.) that no monophosphate remained any more.

After the completion of the reaction, the solvent was distilled off under reduced pressure and the solution was concentrated to 600 ml. This solution was purified by ion exchange chromatography (ion exchange resin: AG501X8, manufactured by BIO-RAD Co.) and the solvent was removed by lyophilizing. Thus 39 g of pure polyethyleneglycol-{2-hydroxy-3-(N-dodecyl-N,N-dimethyl)ammonipropyl}phosphate was obtained in the form of a white powder (isolation yield: 47.4%).

$^1$H-NMR (D$_2$O): δ (ppm):

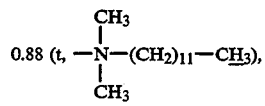

-continued

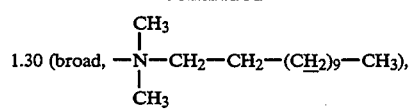

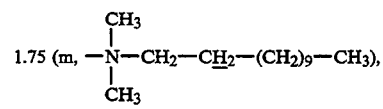

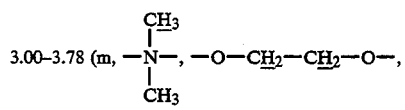

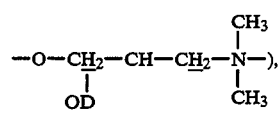

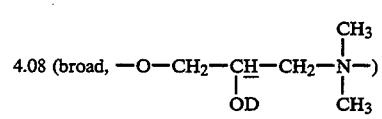

Mass spectrometry (FAB ionization method):
M/Z763(M+H)$^+$(M=C$_{35}$H$_{73}$O$_{14}$NP)

EXAMPLE 33

Synthesis of L-ascorbic acid-2-[{3-(N-dodecyl-N,N-dimethylammonio)-2-hydroxy}propyl]phosphate 10 g (28.4 mmol) of L-ascorbic acid-2-phosphate magnesium salt pentahydrate was introduced into a reaction vessel and dissolved in 250 g of water. After adjusting the pH value to 6.5 with dilute hydrochloric acid, the solution was heated to 60° C. Then a solution of 43 g (141.8 mmol) of glycidyldimethyldodecylammonium chloride dissolved in 100 g of 30% ethanol was slowly added dropwise thereto, while maintaining the reaction system at 60° C. Next, the reaction was carried out at 60° C. for 15 hours. After the completion of the reaction, the solvent was distilled off under reduced pressure and the residue was washed with 10 times of acetone as much as the residue by volume to thereby remove the unreacted glycidyldimethyldodecylammonium chloride and the epoxy-ring opened product thereof. The obtained crude product was washed with 4 times of ethanol as much as the product by volume until a single spot was obtained in thin layer chromatography. Thus 1.8 g of L-ascorbic acid-2-[{3-(N-dodecyl-N,N-dimethylammonio)-2-hydroxy}propyl]phosphate was obtained (isolation yield: 8%).

$^1$H-NMR; δ (ppm); D$_2$O standard 4.5 ppm: 0.55 (s, 3H, a), 1.05 (broad, 18H,b), 1.45 (s, 2H, c), 2.90 (s, 6H, d), 3.0–3.8 (broad, 10H, e), 4.08 (s, 1H, f)

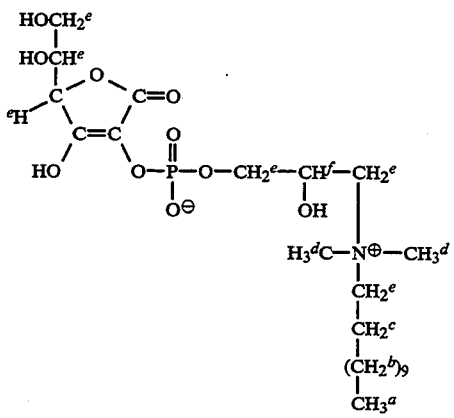

Figure 11:
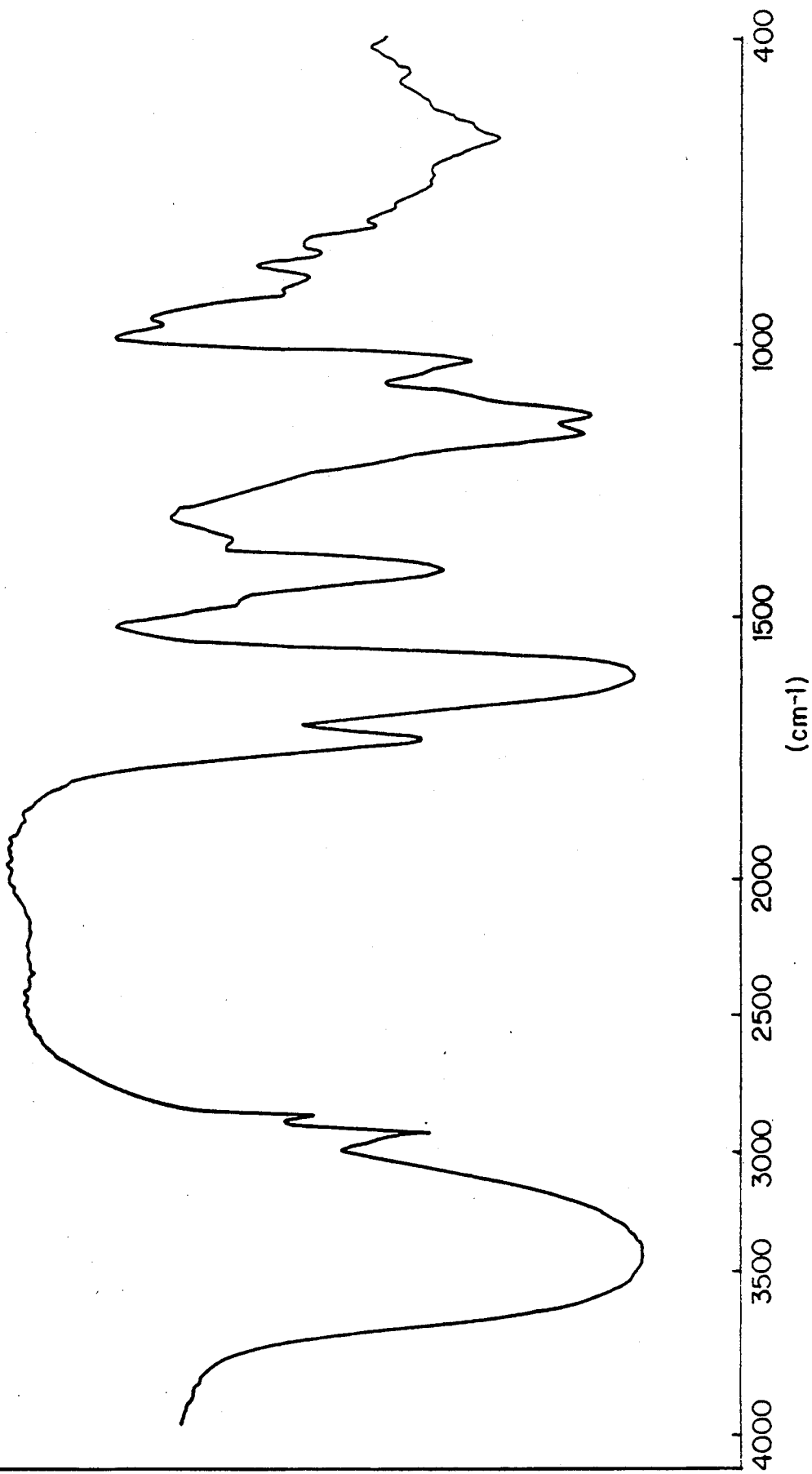
FIG. 11 is the IR spectrum of L-ascorbic acid-2-[{3-(N-dodecyl-N,N-dimethylammonio)-2-hydroxy}propyl]phosphate obtained in Example 33.

IR (KBr pellet method): refer to FIG. 11.

EXAMPLE 34

Synthesis of L-ascorbic acid-2-[{3-(N,N,N-trimethylammonio)-2-hydroxy}propyl]phosphate 10 g (28.4 mmol) of L-ascorbic acid-2-phosphate magnesium salt pentahydrate was introduced into a reaction vessel and dissolved in 250 g of water. After adjusting the pH value to 6.5 with dilute hydrochloric acid, the solution was heated to 60° C. Then a solution of 8.6 g (56.8 mmol) of glycidyltrimethylammonium chloride dissolved in 100 g of 30% ethanol was slowly added dropwise thereto, while maintaining the reaction system at 60° C. Next, the reaction was carried out at 60° C. for 15 hours. After the completion of the reaction, the solvent was distilled off under reduced pressure and the residue was washed with 10 times of acetone as much as the residue by volume to thereby remove the unreacted glycidyltrimethylammonium chloride and the epoxy-ring opened product thereof. The obtained crude product was washed with 4 times of ethanol as much as the product by volume until a single spot was obtained in thin layer chromatography. Thus 0.7 g of L-ascorbic acid-2-[{3-(N,N,N-trimethylammonio)-2-hydroxy}propyl]phosphate was obtained (isolation yield: 7.5%).

$^1$H-NMR; δ (ppm); D$_2$O standard 4.5 ppm: 2.90 (s, 9H, a), 2.9–3.8 (broad, 8H, b), 4.08 (s, 1H, c)

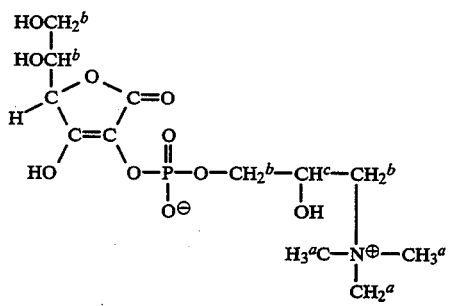

EXAMPLE 35

Synthesis of L-ascorbic acid-6-[{3-(N-dodecyl-N,N-dimethylammonio)-2-hydroxy}propyl]phosphate 10 g (28.4 mmol) of L-ascorbic acid-2-phosphate magnesium salt pentahydrate was introduced into a reaction vessel and dissolved in 250 g of water. After adjusting the pH value to 6.5 with dilute hydrochloric acid, the solution was heated to 60° C. Then a solution of 43 g (141.8 mmol) of glycidyldimethyldodcylammonium chloride dissolved in 100 g of 30% ethanol was slowly added dropwise thereto, while maintaining the reaction system at 60° C. Next, the reaction was carried out at 60° C. for 15 hours. After the completion of the reaction, the solvent was distilled off under reduced pressure and the residue was washed with 10 times of acetone as much as the residue by volume to thereby remove the unreacted glycidyldimethyldodecylammonium chloride and the epoxy-ring opened product thereof. The obtained crude product was washed with 4 times of ethanol as much as the product by volume until a single spot was obtained in thin layer chromatography. Thus 0.9 g of L-ascorbic acid-6-[{3-(N-dodecyl-N,N-dimethylammonio)-2-hydroxy}propyl]phosphate was obtained (isolation yield: 4%).

$^1$H-NMR; δ (ppm); D$_2$O standard 4.5 ppm: 0.54 (s, 3H, a), 1.05 (broad, 18H, b), 1.46 (s, 2H, c), 2.88 (s, 6H, d), 2.90–3.70 (broad, 10H, e), 4.10 (s, 1H, f)

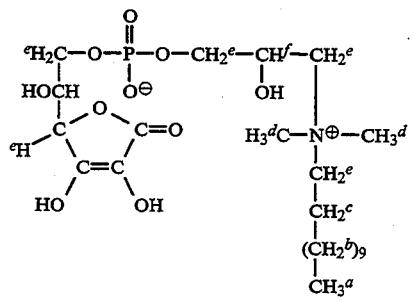

TEST EXAMPLE 2

The solubilities of the L-ascorbic acid-2-[{3-(N-dodecyl-N,N-dimethylammonio)-2-hydroxy}propyl]phosphate obtained in Example 33 in various solvents were examined.

Namely, 50 mg of the compound of the present invention was introduced into a 10 ml test tube and 2 ml of each solvent was added thereto. After shaking, the solubility was evaluated (A: soluble, B: insoluble). Table 2 shows the results.

TABLE 2

| | Water | Ethanol | Glycerol | Propylene glycol |
|---|---|---|---|---|
| Compound of the Invention (Example 33) | A | A | A | A |
| Compound of the Invention (Example 35) | A | A | A | A |
| L-Ascorbic acid-2-phosphate magnesium salt | A | B | B | B |

SYNTHETIC EXAMPLE 6

Synthesis of Sorbitol/cetyl Glycidyl Ether 1 mol Adduct 91 g of sorbitol, 100 g of N-methylpyrrolidone and 1 g of sodium hydroxide as a catalyst were introduced into a reaction vessel and dissolved by heating to 100° C. Then dry nitrogen gas was blown into the reaction vessel so as to distill off water and about 10 g of N-methylpyrrolidone, thus removing the moisture from the reaction system. After adding dropwise 30 g of cetyl glycidyl ether over 2 hours, the mixture was reacted at 110° C. for 4 hours under stirring.

After the completion of the reaction, 1.5 g of acetic acid was added to the reaction mixture to thereby neutralize the catalyst. Then the N-methylpyrrolidone was completely distilled off under reduced pressure at 80° C. 500 g of acetone was added to the residue and the unreacted sorbitol thus precipitated was filtered off. After distilling off the acetone from the filtrate under reduced pressure, 41 g of a crude product of sorbitol/cetyl glycidyl ether 1 mol adduct was obtained.

This crude product was then purified by silica gel chromatography with the use of chloroform/methanol (5:1) as a solvent. The sorbitol/cetyl glycidyl ether 1 mol adduct fractions thus eluted were collected and the solvent was distilled off. Thus 18 g of sorbitol/cetyl glycidyl ether 1 mol adduct was obtained (yield: 37%).

NMR (CDCl$_3$): 67 (ppm) 3.35 ( 15H, m, —O—C$_2$—, O—CH—), 1.15–1.38 ( 28H, m, —CH$_2$—), 0.82 (3H, t, —CH$_3$)

IR (liquid film) cm$^{-1}$; $v_{O-H}$ (—OH): 3200–3400.

SYNTHETIC EXAMPLE 7

Synthesis of Sorbitol Cetylphosphate Sodium Salt 10 g of the sorbitol/cetyl glycidyl ether 1 mol adduct prepared in Synthetic Example 6 and 20 ml of water were introduced into a reaction vessel. Then 3.2 g of phosphorus oxychloride was added dropwise thereto over about 2 hours under stirring at 0° to 5° C. During this period, a 10N aqueous solution of caustic soda was added to the reaction mixture so as to continuously maintain the pH value of the mixture at 13.5. After the completion of the addition of the phosphorus oxychloride, the alkali was further added until no change in pH value was observed any more. The reaction mixture was neutralized with a cation exchange resin (Dowex 50×4H+ type, trade name, manufactured by Dow Chemical Co.) and concentrated under reduced pressure. Then the pH value thereof was adjusted to 10 by adding an aqueous solution of caustic soda. Next, 10 ml of ethanol was added thereto followed by cooling. After removing the inorganic salt thus precipitated, the solvent was, distilled off under reduced pressure. The solution was passed through an electric dialyzer so as to desalt the sodium phosphate. After distilling off water, 6.9 g of purified sorbitol cetylphosphate sodium salt was obtained.

SYNTHETIC EXAMPLE 8

Synthesis of Phosphate of Sorbitol/cetyl Glycidyl Ether Epichlorohydrin Adduct Sodium Salt 10 g of the sorbitol/cetyl glycidyl ether 1 mol adduct prepared in Synthetic Example 6, 30 ml of n-hexane and 0.1 g of trifluoroborane ether complex were introduced into a reaction vessel. Then 2.4 g of epichlorohydrin was added dropwise thereto over about 30 minutes under an inert gas stream, while maintaining the temperature at 20° C. After stirring at room temperature for 1 hour, the reaction mixture was neutralized with a 1N aqueous solution of sodium hydroxide under ice-cooling. The remaining epichlorohydrin was distilled off under reduced pressure with an evaporator and thus 11.9 g of crude monochlorohydrin product was obtained.

This crude product was then dissolved in 20 ml of ethanol and 20 ml of water and a 48% aqueous solution of caustic soda was added thereto until the pH value became constant at 10. Next, a solution of 6.0 g of monosodium phosphate dihydrate dissolved in 20 ml of water was added dropwise thereto over 30 minutes at 60° C.

Then the reaction mixture was aged at 60° C. for 4 hours and the solvent was distilled off under reduced pressure. Thus the aimed crude sorbitol cetylphosphate sodium salt was obtained.

The obtained product was dissolved in a large amount of water and the resulting solution was passed through an electric dialyzer to thereby desalt the unreacted sodium phosphate. After distilling off the water, 10.3 g of purified phosphate of sorbitol/cetyl glycidyl ether epichlorohydrin adduct sodium salt was obtained.

EXAMPLE 36

Synthesis of [3-(N,N,N-trimethylammonio)-2-hydroxypropylphosphate] of sorbitol/cetyl glycidyl ether adduct 8 g of the phosphate of sorbitol/cetyl glycidyl ether adduct sodium salt prepared in Synthetic Example 6, 15 ml of water and 10 ml of ethanol were introduced into a reaction vessel. After adjusting the pH value of the mixture to 7 with 1N hydrochloric acid, 8.7 g of glycidyltrimethylammonium chloride was added thereto at 60° C. under stirring. Then the reaction was carried out at the same temperature for 10 hours.

After the completion of the reaction, the reaction mixture was cooled to room temperature and the solvent was distilled off under reduced pressure. The residue was purified by silica gel column chromatography (chloroform/methanol=1/1 by volume ) to thereby give 3.8 g of pure [3-(N,N,N-trimethylammonio)-2-hydroxypropylphosphate] of sorbitol/cetyl glycidyl ether adduct (yield: 39%).

$^1$H-NMR (D$_2$O): δ (ppm): 0.82 (3H, t, Ha), 1.18–1.37 (28H, m, Hb), 3.26 (9H, s, Hc), 3.33–4.20 (19H, m, Hd+He), 4.40 (1H, m, Hf)

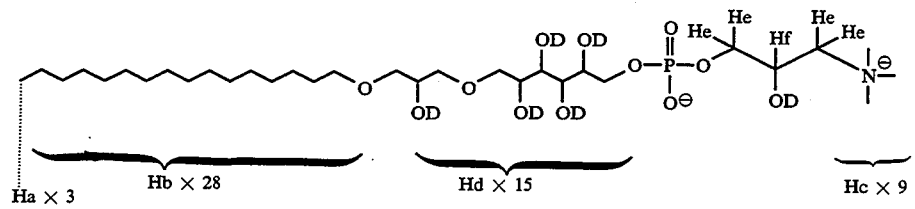

EXAMPLE 37

Synthesis of [3-(N,N,N-trimethylammonio)-2-hydroxypropylphosphate] of sorbitol/cetyl glycidyl ether epichlorohydrin adduct sodium salt 9 g of the phosphate of sorbitol/cetyl glycidyl ether epichlorohydrin adduct sodium salt prepared in Synthetic Example 8, 20 ml of water and 10 ml of ethanol were introduced into a reaction vessel. After adjusting the pH value of the mixture to 7 with 1N hydrochloric acid, 8.7 g of glycidyltrimethylammonium chloride was added thereto at 60° C. under stirring. Then the reaction was carried out at the same temperature for 15 hours.

After the completion of the reaction, the reaction mixture was cooled to room temperature and the solvent was distilled off under reduced pressure. The residue was purified by silica gel column chromatography (chloroform/methanol=1/1 by volume) to thereby give 4.2 g of pure [3-(N,N,N-trimethylammonio)-2-hydroxypropylphosphate] of sorbitol/cetyl glycidyl ether. epichlorohydrin adduct sodium salt (yield: 39%).

$^1$H-NMR (D$_2$O): δ (ppm): 0.81 (3H, t, Ha), 1.13–1.41 (28H, m, Hb), 3.26 (9H, s, Hc), 3.35–4.18 (24H, m, Hd+He), 4.41 (1H, m, Hf)

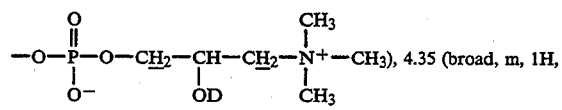, 4.35 (broad, m, 1H,

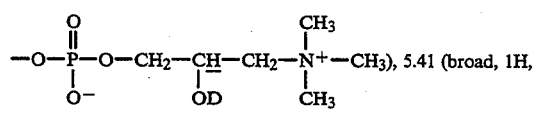, 5.41 (broad, 1H, proton bonding to the anomer carbon of the ribose residue)

EXAMPLE 39

Each detergent composition given in Table 3 was produced and the performances thereof in a hand-wash test and a face-wash test were evaluated by 10 panelists based on the following criteria. Table 1 summarizes the results.

Criteria for Evaluation

Dry-up feeling:
A: no dry-up
B: little dry-up

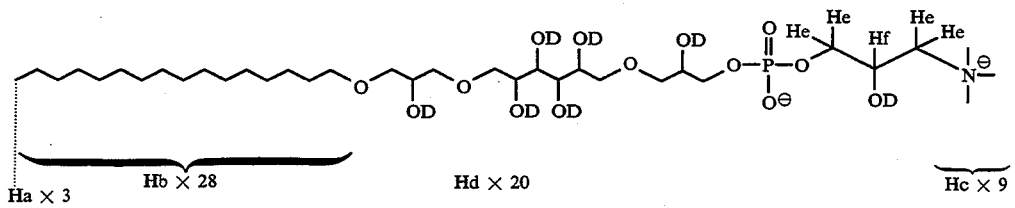

EXAMPLE 38

Synthesis of [3-(N,N,N-trimethylammonio)-2-hydroxypropylphosphate]of sorbitol/cetyl glycidyl ether adduct 8 g of the sorbitol cetylphosphate sodium salt prepared in Synthetic Example 7, 15 ml of water and 10 ml of ethanol were introduced into a reaction vessel. Then 1.5 g of epichlorohydrin was added dropwise thereto over 30 minutes at 60° C. Next, the reaction mixture was stirred at the same temperature for 2 hours and then the pH value thereof was adjusted to 10 with a 48% aqueous solution of sodium hydroxide under ice-cooling.

10 g of a 25% aqueous solution of trimethylamine was added dropwise thereto over 30 minutes, while maintaining the reaction mixture at 10° C. After stirring at the same temperature for 2 hours, the remaining amine and the solvent were distilled off under reduced pressure.

The residue was purified by silica gel column chromatography (chloroform/methanol=1/1 by volume) to thereby give 4.9 g of pure [3-(N,N,N-trimethylammonio)-2-hydroxypropylphosphate] of sorbitol/cetyl glycidyl ether adduct (yield: 50%).

$^1$H-NMR (D$_2$O); δ (ppm):

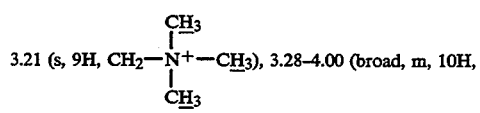, 3.28–4.00 (broad, m, 10H, proton originating from ribose the residue and C: moderate
D: dry-up
Stretched feel:
A: no stretched feel
B: substantially no stretched feel
C: somewhat stretched feel
D: stretched feel
Moist feel:
A: very moist
B: moist
C: moderate
D: dry

TABLE 3

| Component (% by weight) | Product of the Invention | | | Comparative Product 1 |
|---|---|---|---|---|
| | 1 | 2 | 3 | |
| Sodium laurate | 20 | 20 | 20 | 20 |
| Compound obtained in Example 19 | 2 | 5 | — | — |
| Compound obtained in Example 29 | — | — | 2 | — |
| Water | balance | balance | balance | balance |
| Evaluation | | | | |
| Stretched feel | B | A | A | D |
| Dry-up | A | A | B | D |
| Moist feel | A | A | A | D |

Each detergent of the present invention showed an excellent detergency.

EXAMPLE 40

A facial cleansing cream of the following composition was produced.

| Component | Amount (% by weight) |
|---|---|
| Sodium sesquilaurylphosphate | 25 |
| Dipotassium myristylsuccinate | 5 |
| Cocoyl diethanolamide | 2 |
| Polyethyleneglycol monostearate | 4 |
| Compound obtained in Example 14 | 5 |
| Carboxyvinyl polymer | 0.5 |
| Paraben | 0.3 |
| Perfume | 0.3 |
| Purified water | balance |

After washing the face with this product, a refreshing and moist feel remained without any stretched feel.

EXAMPLE 41

A liquid body shampoo of the following composition was produced.

| Component | Amount (% by weight) |
|---|---|
| Triethanolamine laurylphosphate | 20 |
| Alkyl saccharide [$C_{12}$—O—$(G)_{2.5}$]*[1] | 5 |
| Sodium lauroylsarcosinate | 5 |
| Compound obtained in Example 17 | 8 |
| Xanthan gum | 0.5 |
| Propylene glycol | 3 |
| Perfume | 0.7 |
| Purified water | balance |

Note; *[1]: $C_{12}$ means a lauryl group while G means glucose.

After washing with this body shampoo, a moist feel remained without any dry-up feel.

EXAMPLE 42

(Anti-dandruff Shampoo)

| Component | Amount (% by weight) |
|---|---|
| Lauryldimethylaminoacetic acid betaine | 10 |
| Sodium N-lauroylglutamate | 10 |
| pyroctone auramine (octopyrox) | 0.5 |
| Ethylene glycol distearate | 2 |
| Compound obtained in Example 29 | 5 |
| Perfume | 0.5 |
| Water | balance |
| Total | 100 |

This anti-dandruff shampoo gave no creaky feel during shampooing and rinsing and imparted a less sticky but moist feel to the hair after shampooing.

EXAMPLE 43

(Dish Detergent)

| Component | Amount (% by weight) |
|---|---|
| Sodium polyoxyethylene (4) lauryl ether sulfate | 8 |
| Polyoxyethylene (20) myristyl ether | |
| Lauryldimethylamine oxide | 3 |
| Ethanol | 3 |
| Compound of the Invention 6 | 3 |
| Perfume | 0.1 |
| Water | balance |
| Total | 100 |

After washing with this dish detergent, a moist feel remained to the hands with less dry-up feel.

EXAMPLE 44

Each hair rinse composition given in Table 4 was produced. 2 g portions of this composition were applied to the hair of 10 Japanese female panelists, which had been never cold-permed or bleached, after shampooing. Then the hair was rinsed with running water at 40° C. and dried with towel followed by with a dryer. Table 1 summarizes the results of the evaluation for the performance of each composition.

Criteria for Evaluation

Softness:
A: very soft
B: soft
C: moderate
D: hard
Stickiness:
A: absolutely no sticky
B: substantially no sticky
C: moderate
D: sticky
Moist feel:
A: very moist
B: moist
C: moderate
D: dry
Smoothness:
A: very smooth
B: smooth
C: moderate
D: rough

TABLE 4

| Component (% by weight) | Product of the Invention | | | Comparative Product 2 |
|---|---|---|---|---|
| | 4 | 5 | 6 | |
| Stearyltrimethylammonium chloride | 1.3 | 1.3 | 1.3 | 1.3 |
| Cetyl alcohol | 4 | 4 | 4 | 4 |
| Compound obtained in Example 15 | 3 | — | — | — |
| Compound obtained in Example 22 | — | 3 | 5 | — |
| Water | balance | balance | balance | balance |
| Total | 100 | 100 | 100 | 100 |
| Evaluation | | | | |
| Softness | A | A | A | C |
| Stickiness | A | A | A | C |
| Moist feel | A | A | A | C |

EXAMPLE 45

A hair treatment of the following composition was produced.

| Component | Amount (% by weight) |
|---|---|
| (1) 2-Dodecylhexadecyltrimethyl-ammonium chloride | 2 |
| (2) Stearyltrimethylammonium chloride | 2 |
| (3) Compound obtained in Example 36 | 5 |
| (4) Stearyl alcohol | 5 |
| (5) Lanolin | 3 |
| (6) Liquid paraffin | 3 |
| (7) Polypeptide (hydrolysate of collagen) | 5 |
| (8) Hydroxyethyl cellulose (1% aqueous solution, viscosity: 8,000 cp) | 0.5 |
| (9) Polyethylene (5) oleyl ether | 0.5 |
| (10) Methylparaben | 0.2 |
| (11) Perfume | 0.4 |
| (12) Water | balance |
| Total | 100 |

Even after washing away, this hair treatment left to the hair an excellent moisturizing effect and a good moist feel remained to the hair.

EXAMPLE 46

A body treatment of the following composition was produced.

| Component | Amount (% by weight) |
|---|---|
| (1) Arginine 2-hexyldecyl-phosphate | 1 |
| (2) Glycerol-di-2-ethyl-hexanate | 20 |
| (3) Neopentylglycol 2-ethylhexanate | 20 |
| (4) Compound obtained in Example 27 | 5 |
| (5) N-Tris(hydroxymethyl)-isostearic acid amide | 3 |
| (6) Olive oil | 3 |
| (7) Squalane | 3 |
| (8) Sorbitol | 10 |
| (9) Diethylene glycol monoethyl ether | 10 |
| (10) Perfume and colorant | Appropriate amount |
| (11) Water | balance |
| Total | 100 |

Even after washing away, this body treatment left to the skin an excellent moisturizing effect and a good moist feel remained to the skin.

EXAMPLE 47

A cosmetic pack of the following composition was produced.

| Component | Amount (% by weight) |
|---|---|
| (1) Polyvinyl alcohol*1 | 12 |
| (2) Polyethyleneglycol 4000 | 2 |
| (3) Polyoxyethylene methyl glucoside 20 EO adduct*2 | 3 |
| (4) Compound obtained in Example 25 | 5 |
| (5) Squalane | 3 |
| (6) Ethanol | 7.7 |
| (7) Perfume | 0.5 |
| (8) Preservative | Appropriate amount |
| (9) Sorbitan monostearate*3 | 0.5 |
| (10) Polyoxyethylene sorbitan monostearate 20 EO adduct*4 | 0.2 |
| (11) Purified water | balance |

Notes;
*1: Gosenol EG-30, trade name, manufactured by Nippon Gosei Kagaku Kogyo Co., Ltd.
*2: Glucam E-20, trade name, manufactured by Amacoal Corp.
*3: Leodol SPS10, trade name, manufactured by Kao Corp.
*4: Leodol TWS120, trade name, manufactured by Kao Corp.

This cosmetic pack showed an excellent moisturizing effect to the skin which was hard to be removed by perspiration and a good moist feel remained to the skin.

EXAMPLE 48

A cosmetic lotion of the following composition was produced.

| Component | Amount (% by weight) |
|---|---|
| Lactic acid | 0.03 |
| Sodium lactate | 0.84 |
| Compound obtained in Example 31 | 5 |
| Glycerol | 2 |
| Polyoxyethylene oleyl ether 20 EO adduct | 1 |
| Ethanol | 10 |
| Perfume | 0.3 |
| Water | balance |
| Total | 100 |

This cosmetic lotion showed an excellent moisturizing effect to the skin which was hard to be removed by perspiration and a good moist feel remained to the skin.

EXAMPLE 49

A powder bathing preparation of the following composition was produced.

| Component | Amount (% by weight) |
|---|---|
| Sodium hydrogencarbonate | 67 |
| Dextrin | 30 |
| Compound obtained in Example 20 | 2 |
| Perfume | 0.5 |
| Colorant | 0.5 |
| Total | 100 |

This powder bathing preparation showed an excellent moisturizing effect to the skin and a good moist feel remained to the skin after bathing with a bath solution containing this bathing preparation.

EXAMPLE 50

A tablet bathing preparation of the following composition was produced.

| Component | Amount (% by weight) |
|---|---|
| Sodium hydrogencarbonate | 37 |
| Succinic acid | 36 |
| Dextrin | 25 |
| Compound obtained in Example 26 | 1.5 |

| Component | Amount (% by weight) |
|---|---|
| Perfume | 0.5 |
| Total | 100 |

This tablet bathing preparation showed an excellent moisturizing effect to the skin and a good moist feel remained to the skin after bathing with a bath solution containing this bathing preparation.

While the invention has been described in detail and with reference to specific examples thereof, it will be apparent to one skilled in the art that various changes and modifications can be made therein without departing from the spirit and scope thereof.

What is claimed is:

1. A phosphobetaine represented by the following formula (I):

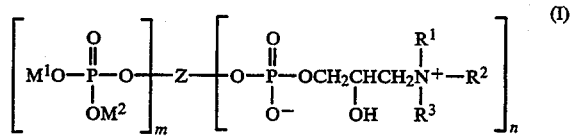

wherein Z represents a residue remaining after eliminating n hydroxyl groups from a polyol selected from the group consisting of the following polyols (a) to (c):

(a) a monosaccharide;
(b) an oligosaccharide; and
(c) a sugar alcohol;

$R^1$, $R^2$ and $R^3$ may be either the same or different from each other and each represents a straight-chain or branched alkyl or alkenyl group having 1 to 24 carbon atoms and optionally having a hydroxyl group; and $M^1$ and $M^2$ may be either the same or different from each other and each represents a hydrogen atom or a cationic group; provided that, when Z is a hexose residue, at least one of $R^1$, $R^2$ and $R^3$ is a straight-chain or branched alkyl or alkenyl group having 5 to 24 carbon atoms and optionally having a hydroxyl group, or a hydroxyalkyl or hydroxyalkenyl group having 1 to 4 carbon atoms;

m is a number of 0 or above; and
n is a number of 1 or above;

provided that the sum of m and n is not more than the number of hydroxy groups in said polyol.

2. The phosphobetaine of claim 1, wherein the polyol is said sugar alcohol (c).

3. A hair treatment composition containing a phosphobetaine represented by Formula (I) set forth in claim 1, and a cosmetically acceptable carrier.

4. A phosphobetaine according to claim 1, wherein at least one of $R^1$, $R^2$ and $R^3$ represents a straight-chain or branched alkyl group having 16 to 24 carbon atoms and optionally having a hydroxyl group and the other two of $R^1$, $R^2$ and $R^3$, which are the same or different from each other, each represents a straight-chain or branched alkyl or alkenyl group having 1 to 24 carbon atoms and optionally having a hydroxyl group.

5. The phosphobetaine according to claim 1, wherein at least one of $R^1$, $R^2$ and $R^3$ represents a straight-chain or branched alkyl group having 12 to 24 carbon atoms and optionally having a hydroxyl group and the other two of $R^1$, $R^2$ and $R^3$, which are the same or different from each other, each represents a straight-chain or branched alkyl or alkenyl group having 1 to 24 carbon atoms and optionally having a hydroxyl group.

6. The phosphobetaine according to claims 4, wherein at least one of $R^1$, $R^2$ and $R^3$ represents a straight-chain or branched alkyl group having 10 to 24 carbon atoms and optionally having a hydroxyl group and the other two of $R^1$, $R^2$ and $R^3$, which are the same or different from each other, each represents a straight-chain or branched alkyl or alkenyl group having 1 to 24 carbon atoms and optionally having a hydroxyl group.

7. The phosphobetaine of any one of claims 4, 5, or 6, wherein the polyol is said sugar alcohol (c).

8. A hair treatment composition containing a phosphobetaine according to any one of claims 4, 5, or 6 and a cosmetically acceptable carrier.

* * * * *